US011787874B2

(12) United States Patent
Lund et al.

(10) Patent No.: US 11,787,874 B2
(45) Date of Patent: Oct. 17, 2023

(54) FACTOR X BINDERS ENHANCING FX ACTIVATION

(71) Applicant: Novo Nordisk A/S, Bagsvaerd (DK)

(72) Inventors: Jacob Lund, Roskilde (DK); Karina Thorn, Farum (DK); Mikkel Nors Harndahl, Roskilde (DK); Marie-Ange Buyse, Merelbeke (BE); Evelyn De Tavernier, Deurle (BE); Soren Steffensen, Etterbeek (BE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/764,124

(22) PCT Filed: Nov. 15, 2018

(86) PCT No.: PCT/EP2018/081296
§ 371 (c)(1),
(2) Date: May 14, 2020

(87) PCT Pub. No.: WO2019/096874
PCT Pub. Date: May 23, 2019

(65) Prior Publication Data

US 2021/0054097 A1 Feb. 25, 2021

(30) Foreign Application Priority Data

Nov. 15, 2017 (EP) .................................... 17201762
May 28, 2018 (EP) .................................... 18174634

(51) Int. Cl.
*C07K 16/36* (2006.01)

(52) U.S. Cl.
CPC .......... *C07K 16/36* (2013.01); *C07K 2317/31* (2013.01); *C07K 2317/34* (2013.01); *C07K 2317/35* (2013.01); *C07K 2317/569* (2013.01); *C07K 2317/75* (2013.01); *C07K 2317/92* (2013.01); *C07K 2317/94* (2013.01)

(58) Field of Classification Search
None
See application file for complete search history.

(56) References Cited

U.S. PATENT DOCUMENTS 8,062,635 B2 11/2011 Hattori et al.
9,334,331 B2 * 5/2016 Igawa .................... C07K 16/36
2007/0041978 A1 2/2007 Hattori et al.
2010/0003254 A1 1/2010 Hattori et al.
2019/0185578 A1 6/2019 Igawa et al.

FOREIGN PATENT DOCUMENTS

EP 3159006 A1 4/2017
WO 9501571 A1 1/1995
WO 0007626 A1 2/2000
WO 2005035753 4/2005
WO 2006109592 11/2008
WO 2009042962 4/2009
WO 2012067176 A1 5/2012
WO 15194233 A1 12/2015
WO 16166014 A1 10/2016
WO 2018047813 3/2018
WO 2018098363 5/2018
WO 2018021450 5/2019

OTHER PUBLICATIONS

Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Ghahroudi et al., FEBS Letters Sep. 15, 1997; 414(3): 521-526.*
Barelle et al., Antibodies 2015, 4, 240-258; doi:10.3390/antib4030240.*
Stanfield et al., J Mol Biol. Mar. 23, 2007;367(2):358-72. doi: 10.1016/j.jmb.2006.12.045. Epub Dec. 22, 2006.*
Juma et al., Cells. May 8, 2021;10(5):1140. doi: 10.3390/cells10051140.*
Yang et al., "Antibodies Against Activated Coagulation Factor X (FXa) in the Antiphospholipid Syndrome that Interfere with the FXa Inactivation by Antithrombin," J Immunol., 2006, vol. 177, pp. 8219-8225.
Zögg T, "Activation Mechanisms of Coagulation Factor IX," Biol Chem, 2009, vol. 390, pp. 391-400.
Artim-Esen et al., "Anti-factor Xa Antibodies in Patients with Antiphosholipid Syndrome and their Effects upon Coagulation Assays," Arthritis Res Ther., 2015, vol. 17, p. 47.
Church et al., "An Inhibitory Monoclonal Antibody to Factor X that Blocks Prothrombin Activation but not Prothrombinase Enzyme Assembly," Blood, vol. 72, pp. 1911-1921.
Fair et al., "Characterization Of 19 Monoclonal-Antibodies To Human Factor-X," Thrombosis And Haemostasis, 1985, vol. 54, Issue 1, p. 149.
Kolkman JA et al., "Insertion Loop 256-268 in Coagulation Factor IX Restricts Enzymatic Activity in the Absence but Not in the Presence of Factor VIII," Biochemistry, 2000, vol. 39, pp. 7398-7405.
Ouellette et al., "Neutralization of Factor X Activity by Factor-X Specific Monoclonal Antibodies," Blood coagulation and Fibrinolysis, 1992, vol. 3, pp. 563-574.
Scheiflinger et al., "Enhancement of the enzymatic activity of activated coagulation factor IX by anti-factor IX antibodies," J Thromb Haemost, 2008, vol. 6, pp. 315-322.
Tang et al., "Generation And Characterization Of A Monoclonal-Antibody To Human Factor-X Which Depletes Greater-Than 99-Percent Factor-X Activity In Plasma," Thrombosis And Haemostasis, 1993, vol. 69, Issue 6, p. 617.

(Continued)

*Primary Examiner* — Michael Szperka
(74) *Attorney, Agent, or Firm* — Jianjie Hu

(57) ABSTRACT

The application relates to unique FX binding molecules, such as antibodies and fragments thereof which are useful in the treatment of haemophilia.

7 Claims, No Drawings

Specification includes a Sequence Listing.

(56) References Cited

OTHER PUBLICATIONS

Sampei et al., "Identification and Multidimensional Optimization of an Asymmetric Bispecific IgG Antibody Mimicking the Function of Factor VIII Cofactor Activity", PLOS ONE, Feb. 28, 2013, vol. 8, No. 2, e57479, pp. 1-13.
Kitazawa et al.,"A bispecific antibody to factors IXa and X restores factor VIII hemostatic activity in a hemophilia A model" Nature Medicine, 2012, vol. 18, No. 10, pp. 1570-1574.
Kitazawa et al., "Factor VIIIa-mimetic cofactor activity of a bispecific antibody to factors IX/IXa and X/Xa, emicizumab, depends on its ability to bridge the antigens", Thrombosis and Haemostasis, Jul. 2017, vol. 117, No. 07, pp. 1348-1357.

* cited by examiner

SEQUENCE LISTING

```
<160> NUMBER OF SEQ ID NOS: 57

<210> SEQ ID NO 1
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285
```

-continued

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 2
<211> LENGTH: 448
<212> TYPE: PRT
<213> ORGANISM: Homo sapiens

<400> SEQUENCE: 2

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu

-continued

```
            245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445


<210> SEQ ID NO 3
<211> LENGTH: 2
<212> TYPE: PRT
<213> ORGANISM: Artificial Sequence
<220> FEATURE:
<223> OTHER INFORMATION: Common mimimal epitope

<400> SEQUENCE: 3

Leu Leu
1


<210> SEQ ID NO 4
<211> LENGTH: 117
<212> TYPE: PRT
<213> ORGANISM: Homo sapiens
<220> FEATURE:
<223> OTHER INFORMATION: Antibody heavy chain variable domain

<400> SEQUENCE: 4

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Thr Ser Gly Ser Thr Phe Tyr Ala Thr Trp Ala Lys Gly
    50                  55                  60

Arg Phe Thr Ile Ser Lys Thr Ser Thr Thr Val Asp Leu Lys Ile Ile
65                  70                  75                  80

Ser Pro Thr Ile Glu Asp Thr Ala Thr Tyr Phe Cys Ala Arg Asp Met
                85                  90                  95
```

-continued

```
Trp Ala Gly Ser Arg Tyr Asp Phe Asn Ile Trp Gly Pro Gly Thr Leu
            100                 105                 110

Val Thr Val Ser Ser
        115


<210> SEQ ID NO 5
<211> LENGTH: 113
<212> TYPE: PRT
<213> ORGANISM: Artificial Sequence
<220> FEATURE:
<223> OTHER INFORMATION: Antibody light chain variable domain

<400> SEQUENCE: 5

Ala Asp Ile Val Met Thr Gln Thr Pro Ala Ser Val Glu Ala Ala Val
1               5                   10                  15

Gly Gly Thr Val Thr Ile Lys Cys Gln Ala Ser Gln Ser Ile Ser Ser
            20                  25                  30

Tyr Leu Ala Trp Tyr Gln Gln Lys Pro Gly Gln Arg Pro Lys Leu Leu
        35                  40                  45

Ile Tyr Arg Ala Ser Thr Leu Glu Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Thr Tyr Tyr Tyr Ser Gly
                85                  90                  95

Gly Gly Ser Tyr Ala Ser Ala Phe Gly Gly Gly Thr Glu Val Val Val
            100                 105                 110

Lys


<210> SEQ ID NO 6
<211> LENGTH: 117
<212> TYPE: PRT
<213> ORGANISM: Artificial Sequence
<220> FEATURE:
<223> OTHER INFORMATION: Antibody heavy chain variable domain

<400> SEQUENCE: 6

Glu Val Gln Leu Val Glu Ser Gly Gly Gly Gln Val Lys Pro Gly Gly
1               5                   10                  15

Ser Leu Arg Leu Ser Cys Ala Ala Ser Gly Phe Thr Phe Ser Thr Ser
            20                  25                  30

Ser Ile Tyr Trp Val Arg Gln Ala Pro Gly Lys Gly Leu Glu Trp Val
        35                  40                  45

Ser Ser Ile Ser Ser Gly Ser Ser Tyr Ile Phe Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Val Ser Gly Tyr Ser Arg Leu Leu Asp Tyr Trp Gly Gln Gly Thr Leu
            100                 105                 110

Val Thr Val Ser Ser
        115


<210> SEQ ID NO 7
<211> LENGTH: 112
<212> TYPE: PRT
<213> ORGANISM: Artificial Sequence
<220> FEATURE:
```

<223> OTHER INFORMATION: Antibody light chain variable domain

<400> SEQUENCE: 7

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Gly
                85                  90                  95

Thr His Trp Pro Leu Thr Phe Gly Gly Gly Thr Lys Val Glu Ile Lys
            100                 105                 110
```

<210> SEQ ID NO 8
<211> LENGTH: 120
<212> TYPE: PRT
<213> ORGANISM: Artificial Sequence
<220> FEATURE:
<223> OTHER INFORMATION: Single variable domain antibody

<400> SEQUENCE: 8

```
Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Ala Thr Pro Ala Asn Gly Glu Leu Asp Tyr Trp Gly Gln
            100                 105                 110

Gly Thr Leu Val Thr Val Ser Ser
        115                 120
```

<210> SEQ ID NO 9
<211> LENGTH: 120
<212> TYPE: PRT
<213> ORGANISM: Artificial Sequence
<220> FEATURE:
<223> OTHER INFORMATION: Single variable domain antibody

<400> SEQUENCE: 9

```
Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Arg Arg Gly Gly Arg Thr Tyr Tyr Ala Asp Ser Val
```

```
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Ala Thr Ala Arg Asp Gly Leu Leu Asp Tyr Trp Gly Gln
            100                 105                 110

Gly Thr Leu Val Thr Val Ser Ser
        115                 120


<210> SEQ ID NO 10
<211> LENGTH: 120
<212> TYPE: PRT
<213> ORGANISM: Artificial Sequence
<220> FEATURE:
<223> OTHER INFORMATION: Single variable domain antibody

<400> SEQUENCE: 10

Glu Val Gln Leu Val Glu Ser Gly Gly Gly Val Val Gln Pro Gly Gly
1               5                   10                  15

Ser Leu Arg Leu Ser Cys Val Ala Ser Gly Arg Thr Phe Ser Arg Tyr
            20                  25                  30

Ala Met Gly Trp Phe Arg Gln Ala Pro Gly Lys Glu Arg Glu Phe Val
        35                  40                  45

Ala Ala Ile Ser Arg Arg Gly Gly Ser Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Tyr Ser Ser Gly Asp Gly Tyr Leu Asp Tyr Trp Gly Gln
            100                 105                 110

Gly Thr Leu Val Thr Val Ser Ser
        115                 120


<210> SEQ ID NO 11
<211> LENGTH: 120
<212> TYPE: PRT
<213> ORGANISM: Artificial Sequence
<220> FEATURE:
<223> OTHER INFORMATION: Single variable domain antibody

<400> SEQUENCE: 11

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Leu Ser Arg Tyr
            20                  25                  30

Ala Met Gly Trp Phe Arg Gln Ala Pro Gly Lys Glu Arg Glu Phe Val
        35                  40                  45

Ala Ala Ile Thr Arg Arg Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Leu Ala Pro Gly Asp Tyr Ala Leu Asp Tyr Trp Gly Gln
            100                 105                 110
```

-continued

```
Gly Thr Leu Val Thr Val Ser Ser
        115                 120


<210> SEQ ID NO 12
<211> LENGTH: 121
<212> TYPE: PRT
<213> ORGANISM: Artificial Sequence
<220> FEATURE:
<223> OTHER INFORMATION: Single variable domain antibody

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Asp Ile Gly Ser Gly Gly Gly Val Ser Thr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Met Tyr Tyr
                85                  90                  95

Cys Ala Arg Gly Trp Thr Tyr Gly Ser Asp Gly Met Asp Tyr Trp Gly
            100                 105                 110

Lys Gly Thr Leu Val Thr Val Ser Ser
        115                 120


<210> SEQ ID NO 13
<211> LENGTH: 12
<212> TYPE: PRT
<213> ORGANISM: Human

<400> SEQUENCE: 13

Ser Val Ala Gln Ala Thr Ser Ser Ser Gly Glu Ala
1               5                   10


<210> SEQ ID NO 14
<211> LENGTH: 12
<212> TYPE: PRT
<213> ORGANISM: Human

<400> SEQUENCE: 14

Val Ala Gln Ala Thr Ser Ser Ser Gly Glu Ala Pro
1               5                   10


<210> SEQ ID NO 15
<211> LENGTH: 12
<212> TYPE: PRT
<213> ORGANISM: Human

<400> SEQUENCE: 15

Ala Gln Ala Thr Ser Ser Ser Gly Glu Ala Pro Asp
1               5                   10


<210> SEQ ID NO 16
<211> LENGTH: 12
<212> TYPE: PRT
<213> ORGANISM: Human

<400> SEQUENCE: 16

Gln Ala Thr Ser Ser Ser Gly Glu Ala Pro Asp Ser
```

-continued 1 5 10

<210> SEQ ID NO 17
<211> LENGTH: 12
<212> TYPE: PRT
<213> ORGANISM: Human

<400> SEQUENCE: 17

Ala Thr Ser Ser Ser Gly Glu Ala Pro Asp Ser Ile
1 5 10

<210> SEQ ID NO 18
<211> LENGTH: 12
<212> TYPE: PRT
<213> ORGANISM: Human

<400> SEQUENCE: 18

Thr Ser Ser Ser Gly Glu Ala Pro Asp Ser Ile Thr
1 5 10

<210> SEQ ID NO 19
<211> LENGTH: 12
<212> TYPE: PRT
<213> ORGANISM: Human

<400> SEQUENCE: 19

Ser Ser Ser Gly Glu Ala Pro Asp Ser Ile Thr Trp
1 5 10

<210> SEQ ID NO 20
<211> LENGTH: 12
<212> TYPE: PRT
<213> ORGANISM: Human

<400> SEQUENCE: 20

Ser Ser Gly Glu Ala Pro Asp Ser Ile Thr Trp Lys
1 5 10

<210> SEQ ID NO 21
<211> LENGTH: 12
<212> TYPE: PRT
<213> ORGANISM: Human

<400> SEQUENCE: 21

Ser Gly Glu Ala Pro Asp Ser Ile Thr Trp Lys Pro
1 5 10

<210> SEQ ID NO 22
<211> LENGTH: 12
<212> TYPE: PRT
<213> ORGANISM: Human

<400> SEQUENCE: 22

Gly Glu Ala Pro Asp Ser Ile Thr Trp Lys Pro Tyr
1 5 10

<210> SEQ ID NO 23
<211> LENGTH: 12
<212> TYPE: PRT
<213> ORGANISM: Human

<400> SEQUENCE: 23

Glu Ala Pro Asp Ser Ile Thr Trp Lys Pro Tyr Asp
1 5 10

<210> SEQ ID NO 24
<211> LENGTH: 12
<212> TYPE: PRT
<213> ORGANISM: Human

<400> SEQUENCE: 24

Ala Pro Asp Ser Ile Thr Trp Lys Pro Tyr Asp Ala
1 5 10

<210> SEQ ID NO 25
<211> LENGTH: 12
<212> TYPE: PRT
<213> ORGANISM: Human

<400> SEQUENCE: 25

Pro Asp Ser Ile Thr Trp Lys Pro Tyr Asp Ala Ala
1 5 10

<210> SEQ ID NO 26
<211> LENGTH: 12
<212> TYPE: PRT
<213> ORGANISM: Human

<400> SEQUENCE: 26

Asp Ser Ile Thr Trp Lys Pro Tyr Asp Ala Ala Asp
1 5 10

<210> SEQ ID NO 27
<211> LENGTH: 12
<212> TYPE: PRT
<213> ORGANISM: Human

<400> SEQUENCE: 27

Ser Ile Thr Trp Lys Pro Tyr Asp Ala Ala Asp Leu
1 5 10

<210> SEQ ID NO 28
<211> LENGTH: 12
<212> TYPE: PRT
<213> ORGANISM: Human

<400> SEQUENCE: 28

Ile Thr Trp Lys Pro Tyr Asp Ala Ala Asp Leu Asp
1 5 10

<210> SEQ ID NO 29
<211> LENGTH: 12
<212> TYPE: PRT
<213> ORGANISM: Human

<400> SEQUENCE: 29

Thr Trp Lys Pro Tyr Asp Ala Ala Asp Leu Asp Pro
1 5 10

<210> SEQ ID NO 30
<211> LENGTH: 12
<212> TYPE: PRT
<213> ORGANISM: Human

<400> SEQUENCE: 30

Trp Lys Pro Tyr Asp Ala Ala Asp Leu Asp Pro Thr
1 5 10

<210> SEQ ID NO 31

<211> LENGTH: 12
<212> TYPE: PRT
<213> ORGANISM: Human

<400> SEQUENCE: 31

Lys Pro Tyr Asp Ala Ala Asp Leu Asp Pro Thr Glu
1 5 10

<210> SEQ ID NO 32
<211> LENGTH: 12
<212> TYPE: PRT
<213> ORGANISM: Human

<400> SEQUENCE: 32

Pro Tyr Asp Ala Ala Asp Leu Asp Pro Thr Glu Asn
1 5 10

<210> SEQ ID NO 33
<211> LENGTH: 12
<212> TYPE: PRT
<213> ORGANISM: Human

<400> SEQUENCE: 33

Tyr Asp Ala Ala Asp Leu Asp Pro Thr Glu Asn Pro
1 5 10

<210> SEQ ID NO 34
<211> LENGTH: 12
<212> TYPE: PRT
<213> ORGANISM: Human

<400> SEQUENCE: 34

Asp Ala Ala Asp Leu Asp Pro Thr Glu Asn Pro Phe
1 5 10

<210> SEQ ID NO 35
<211> LENGTH: 12
<212> TYPE: PRT
<213> ORGANISM: Human

<400> SEQUENCE: 35

Ala Ala Asp Leu Asp Pro Thr Glu Asn Pro Phe Asp
1 5 10

<210> SEQ ID NO 36
<211> LENGTH: 12
<212> TYPE: PRT
<213> ORGANISM: Human

<400> SEQUENCE: 36

Ala Asp Leu Asp Pro Thr Glu Asn Pro Phe Asp Leu
1 5 10

<210> SEQ ID NO 37
<211> LENGTH: 12
<212> TYPE: PRT
<213> ORGANISM: Human

<400> SEQUENCE: 37

Asp Leu Asp Pro Thr Glu Asn Pro Phe Asp Leu Leu
1 5 10

<210> SEQ ID NO 38
<211> LENGTH: 12
<212> TYPE: PRT

<213> ORGANISM: Human

<400> SEQUENCE: 38

Leu Asp Pro Thr Glu Asn Pro Phe Asp Leu Leu Asp
1 5 10

<210> SEQ ID NO 39
<211> LENGTH: 12
<212> TYPE: PRT
<213> ORGANISM: Human

<400> SEQUENCE: 39

Asp Pro Thr Glu Asn Pro Phe Asp Leu Leu Asp Phe
1 5 10

<210> SEQ ID NO 40
<211> LENGTH: 12
<212> TYPE: PRT
<213> ORGANISM: Human

<400> SEQUENCE: 40

Pro Thr Glu Asn Pro Phe Asp Leu Leu Asp Phe Asn
1 5 10

<210> SEQ ID NO 41
<211> LENGTH: 12
<212> TYPE: PRT
<213> ORGANISM: Human

<400> SEQUENCE: 41

Thr Glu Asn Pro Phe Asp Leu Leu Asp Phe Asn Gln
1 5 10

<210> SEQ ID NO 42
<211> LENGTH: 12
<212> TYPE: PRT
<213> ORGANISM: Human

<400> SEQUENCE: 42

Glu Asn Pro Phe Asp Leu Leu Asp Phe Asn Gln Thr
1 5 10

<210> SEQ ID NO 43
<211> LENGTH: 12
<212> TYPE: PRT
<213> ORGANISM: Human

<400> SEQUENCE: 43

Asn Pro Phe Asp Leu Leu Asp Phe Asn Gln Thr Gln
1 5 10

<210> SEQ ID NO 44
<211> LENGTH: 12
<212> TYPE: PRT
<213> ORGANISM: Human

<400> SEQUENCE: 44

Pro Phe Asp Leu Leu Asp Phe Asn Gln Thr Gln Pro
1 5 10

<210> SEQ ID NO 45
<211> LENGTH: 12
<212> TYPE: PRT
<213> ORGANISM: Human

<400> SEQUENCE: 45

Phe Asp Leu Leu Asp Phe Asn Gln Thr Gln Pro Glu
1 5 10

<210> SEQ ID NO 46
<211> LENGTH: 12
<212> TYPE: PRT
<213> ORGANISM: Human

<400> SEQUENCE: 46

Asp Leu Leu Asp Phe Asn Gln Thr Gln Pro Glu Arg
1 5 10

<210> SEQ ID NO 47
<211> LENGTH: 12
<212> TYPE: PRT
<213> ORGANISM: Human

<400> SEQUENCE: 47

Leu Leu Asp Phe Asn Gln Thr Gln Pro Glu Arg Gly
1 5 10

<210> SEQ ID NO 48
<211> LENGTH: 12
<212> TYPE: PRT
<213> ORGANISM: Human

<400> SEQUENCE: 48

Leu Asp Phe Asn Gln Thr Gln Pro Glu Arg Gly Asp
1 5 10

<210> SEQ ID NO 49
<211> LENGTH: 12
<212> TYPE: PRT
<213> ORGANISM: Human

<400> SEQUENCE: 49

Asp Phe Asn Gln Thr Gln Pro Glu Arg Gly Asp Asn
1 5 10

<210> SEQ ID NO 50
<211> LENGTH: 12
<212> TYPE: PRT
<213> ORGANISM: Human

<400> SEQUENCE: 50

Phe Asn Gln Thr Gln Pro Glu Arg Gly Asp Asn Asn
1 5 10

<210> SEQ ID NO 51
<211> LENGTH: 12
<212> TYPE: PRT
<213> ORGANISM: Human

<400> SEQUENCE: 51

Asn Gln Thr Gln Pro Glu Arg Gly Asp Asn Asn Leu
1 5 10

<210> SEQ ID NO 52
<211> LENGTH: 12
<212> TYPE: PRT
<213> ORGANISM: Human

<400> SEQUENCE: 52

-continued

```
Gln Thr Gln Pro Glu Arg Gly Asp Asn Asn Leu Thr
1               5                   10


<210> SEQ ID NO 53
<211> LENGTH: 12
<212> TYPE: PRT
<213> ORGANISM: Human

<400> SEQUENCE: 53

Thr Gln Pro Glu Arg Gly Asp Asn Asn Leu Thr Arg
1               5                   10


<210> SEQ ID NO 54
<211> LENGTH: 120
<212> TYPE: PRT
<213> ORGANISM: Artificial
<220> FEATURE:
<223> OTHER INFORMATION: Single variable domain antibody

<400> SEQUENCE: 54

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Thr Tyr
            20                  25                  30

Ser Met Gly Trp Phe Arg Gln Ala Pro Gly Lys Glu Arg Glu Phe Val
        35                  40                  45

Ala Ala Ile Thr Arg Arg Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Arg Arg Pro Ala Asp Ser Tyr Leu Asp Tyr Trp Gly Gln
            100                 105                 110

Gly Thr Leu Val Thr Val Ser Ser
        115                 120


<210> SEQ ID NO 55
<211> LENGTH: 121
<212> TYPE: PRT
<213> ORGANISM: Artificial sequence
<220> FEATURE:
<223> OTHER INFORMATION: Single variable domain antibody

<400> SEQUENCE: 55

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Thr Ser Gly Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Ala Val Arg Thr Leu Gly Leu Arg Gly Ser Tyr Asp Tyr Trp Gly
            100                 105                 110
```

-continued

```
Gln Gly Thr Leu Val Thr Val Ser Ser
        115                 120


<210> SEQ ID NO 56
<211> LENGTH: 120
<212> TYPE: PRT
<213> ORGANISM: Artificial sequence
<220> FEATURE:
<223> OTHER INFORMATION: Single variable domain antibody

<400> SEQUENCE: 56

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Thr Gly Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Leu Tyr Tyr Cys Ala
                85                  90                  95

Ala Ala Ile Leu Thr Arg Thr Arg Arg Thr Tyr Asp Tyr Trp Gly Gln
            100                 105                 110

Gly Thr Leu Val Thr Val Ser Ser
        115                 120


<210> SEQ ID NO 57
<211> LENGTH: 121
<212> TYPE: PRT
<213> ORGANISM: Artificial sequence
<220> FEATURE:
<223> OTHER INFORMATION: Single variable domain antibody

<400> SEQUENCE: 57

Glu Val Gln Leu Val Glu Ser Gly Gly Gly Val Val Gln Pro Gly Gly
1               5                   10                  15

Ser Leu Arg Leu Ser Cys Val Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Thr Ser Gly Ser Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Ala Ile Leu Arg Gly Tyr Arg Lys Thr Tyr Asp Tyr Trp Gly
            100                 105                 110

Gln Gly Thr Leu Val Thr Val Ser Ser
        115                 120
```

FACTOR X BINDERS ENHANCING FX ACTIVATION

CROSS-REFERENCE TO RELATED APPLICATIONS

This application is a 35 U.S.C. § 371 National Stage application of International Application PCT/EP2018/081296 (WO 2019/096874), filed Nov. 15, 2018, which claims priority to European Patent Application 17201762.6, filed Nov. 15, 2017 and European Patent Application 18174634.8, filed May 28, 2018; the contents of which are incorporated herein by reference.

TECHNICAL FIELD OF THE INVENTION

The invention relates to coagulation Factor X binders and their use in the treatment of coagulopathy, such as haemophilia.

INCORPORATION-BY-REFERENCE OF THE SEQUENCE LISTING

The present application is filed with a Sequence Listing in electronic form. The entire contents of the sequence listing are hereby incorporated by reference.

BACKGROUND

In patients with a coagulopathy, such as in human beings with haemophilia A and B, various steps of the coagulation cascade are rendered dysfunctional due to, for example, the absence or insufficient presence of a coagulation factor. Such dysfunction of one part of the coagulation cascade results in insufficient blood coagulation and potentially life-threatening bleeding, or damage to internal organs, such as the joints.

Coagulation Factor VIII (FVIII) deficiency, commonly referred to as haemophilia A, is a congenital bleeding disorder affecting approximately 420,000 people worldwide, of which around 105,000 are currently diagnosed.

Patients with haemophilia A may receive coagulation factor replacement therapy such as exogenous FVIII. Conventional treatment consists of replacement therapy, provided as prophylaxis or on demand treatment of bleeding episodes. The current standard of care for a patient with severe haemophilia A is up to three prophylactic intravenous injections/week with either plasma-derived FVIII or recombinant FVIII or long-acting variants thereof.

However, such patients are at risk of developing neutralizing antibodies, so-called "inhibitors", to such exogenous factors, rendering formerly efficient therapy ineffective. Haemophilia A patients with "inhibitors" (that is, allo-antibodies against FVIII) is a non-limiting example of a coagulopathy that is partly congenital and partly acquired. Patients that have developed "inhibitors" to FVIII are unable to receive conventional replacement therapy, either as prophylaxis or on demand.

Furthermore, exogenous coagulation factors may only be administered intravenously, which is of considerable inconvenience and discomfort to patients. For example, infants and toddlers may have to have intravenous catheters surgically inserted into a chest vein, in order for venous access to be guaranteed. This leaves them at great risk of developing bacterial infections.

In a bleeding individual, coagulation is initiated by the Tissue Factor/Factor VIIa (TF/FVIIa) complex when extravascular TF is exposed to activated FVII (FVIIa) in the blood. TF/FVIIa complex formation leads to the activation of Factor X (FX) to activated Factor Xa (FXa) which, together with activated Factor V (FVa), generates a limited amount of thrombin.

Small amounts of thrombin activate platelets. Activated platelets support the assembly and binding of the tenase complex composed of activated Factor VIII (FVIIIa) and activated Factor IX (FIXa). The tenase complex is a very efficient catalyst of FX activation and FXa generated in this second step serves as the active protease in the FVa/FXa pro-thrombinase complex which is responsible for the final thrombin burst. Thrombin cleaves fibrinogen to generate fibrin monomers, which polymerise to form a fibrin network which seals the leaking vessel and stops the bleeding. The rapid and extensive thrombin burst is a prerequisite for the formation of a solid and stable fibrin clot.

An inadequate FXa formation and decreased thrombin generation caused by absence of coagulation Factor FVIII activity is the reason underlying the bleeding diathesis in haemophilia A patients.

As mentioned, proteolytic conversion of FX into its enzymatically active form FXa can be achieved by the intrinsic FX-activating complex comprising FIXa and its cofactor FVIIIa. Cofactor binding increases the enzymatic activity of FIXa by about five orders of magnitude and is believed to result through multiple mechanisms as outlined by Scheiflinger et al. (2008) *J Thromb Haemost,* 6:315-322. Notably, FVIIIa has been found to stabilize a conformation of FIXa that has increased proteolytic activity towards FX (Kolkman J A, Mertens K (2000) *Biochemistry,* 39:7398-7405, Zögg T, Brandstetter H (2009) *Biol Chem,* 390:391-400). Based on this observation and realizing that antibodies are versatile binding proteins capable of mimicking a variety of protein-protein interactions, Scheiflinger et al. performed a screen for agonistic anti-FIXa antibodies characterized by an ability to enhance FX activation by FIXa in the presence of a phospholipid surface and calcium, but the absence of the natural cofactor FVIIIa. From a screen of 5280 hybridoma supernatants, 88 antibodies were found to exhibit different degrees of FIXa agonistic activity.

Antibodies binding to Factor X/Xa have previously been characterized (U.S. Pat. No. 8,062,635) and emicizumab also known as ACE910 (U.S. Pat. No. 9,334,331) is approved as a by-passing agent mimicking the action of FVIIIa by binding to Factor IX/IXa with one arm and factor X/Xa with the other. The anti-FX arm of emicizumab binds the light chain of FX and is not specific for the zymogen form but rather binds FX and FXa with comparable affinities. The anti-FX arm is believed mainly to recruit FX and bring it close to FIXa.

Thus, while mimicking the overall activity of FVIIIa, the FVIII mimetic compound emicizumab appears to lack some of the inherent specificity and functions of FVIIIa. Specifically, FVIIIa works by binding FIXa and zymogen FX on a phospholipid surface, enhancing FX-activation by stimulating FIXa activity by approximately 200,000-fold and subsequently releasing FXa.

Variants of ACE910 stated to have functional improvements are disclosed in WO2018/021450. Further bispecific anti-FIX/anti-FX FVIII mimetic compounds are disclosed in WO2018/098363 The present invention relates to FX binders stimulating the generation of FXa. Such molecules are thus of potential therapeutic use either as individual compounds or as a component of a FVIII mimicking compound.

SUMMARY

The present invention relates to a group of FX binders, such as FX antibodies or fragments thereof which are capable of stimulating FX activation, i.e. the generation of FXa from FX, as well as the identification of such FX binders.

The present invention further relates to a group of FX binders, including antibodies and antigen-binding fragments thereof, including immunoglobulin single variable domains, such as Nanobodies®, capable of binding to zymogen FX and not the activated FX (FXa).

The binding of FX by the FX binders disclosed herein stimulates subsequent activation of FX by FIXa. In one aspect, the binding occurs via a peptide stretch in activating peptide of FX. It has thus been observed that the FX binders disclosed herein stimulate FX activation by making FX more prone to FIXa-mediated activation.

In one aspect, specific binding of the zymogen form of FX relative to the activated form (FXa) prevent sequestering of the FX binder on generated FXa, thereby increasing the amount of FX binder available for interaction with zymogen FX. Furthermore, specific binding to zymogen FX avoids potential inhibitory effects on FXa activity (such as interference with assembly of the prothrombinase complex).

The FX binders disclosed herein display unexpected functional properties by binding to FX in a manner that makes FX more prone to proteolysis by FIXa. It is a surprising finding by the inventors that increased proteolysis of FX by FIXa can be accomplished by binding of FX in a manner that makes it more prone to proteolysis and consequent activation by FIXa. There are examples in the art of anti-FIXa compounds stimulating FIXa proteolytic activity for conversion of FX into FXa. However, there are to our knowledge, no prior knowledge of compounds capable of binding to FX and stimulating FX activation by making FX more prone to proteolysis by FIXa.

An aspect of the invention relates to a FX binder, such as an antibody or antigen-binding fragment thereof, binding to FX, wherein the antibody or antigen-binding fragment thereof is capable of stimulating FX activation. Another aspect of the invention relates to the identification of such compounds.

Further aspects of the invention relates to the use of such FX binders, possibly, but not exclusively as part of a FVIII mimetic compound, in methods of treatment. Stimulation of FX activation is useful for stimulation of coagulation, and such molecules are thus suitable for treatment of coagulopathies such as haemophilia, including haemophilia A and B.

OVERVIEW OF SEQUENCE LISTING human Factor IX zymogen

SEQ ID NO: 1

```
YNSGKLEEFV QGNLERECME EKCSFEEARE VFENTERTTE FWKQYVDGDQ CESNPCLNGG  60

SCKDDINSYE CWCPFGFEGK NCELDVTCNI KNGRCEQFCK NSADNKVVCS CTEGYRLAEN 120

QKSCEPAVPF PCGRVSVSQT SKLTRAEAVF PDVDYVNSTE AETILDNITQ STQSFNDFTR 180

VVGGEDAKPG QFPWQVVLNG KVDAFCGGSI VNEKWIVTAA HCVETGVKIT VVAGEHNIEE 240

TEHTEQKRNV IRIIPHHNYN AAINKYNHDI ALLELDEPLV LNSYVTPICI ADKEYTNIFL 300

KFGSGYVSGW GRVFHKGRSA LVLQYLRVPL VDRATCLRST KFTIYNNMFC AGFHEGGRDS 360

CQGDSGGPHV TEVEGTSFLT GIISWGEECA MKGKYGIYTK VSRYVNWIKE KTKLT
```

human Factor X zymogen

SEQ ID NO: 2

ANSFLEEMKK GHLERECMEE TCSYEEAREV FEDSDKTNEF WNKYKDGDQC ETSPCQNQGK 60

CKDGLGEYTC TCLEGFEGKN CELFTRKLCS LDNGDCDQFC HEEQNSVVCS CARGYTLADN 120

GKACIPTGPY PCGKQTLERR KR<u>SVAQATSS SGEAPDSITW KPYDAADLDP TENPFDLLDF</u> 180

<u>NQTQPERGDN NLTR</u>IVGGQE CKDGECPWQA LLINEENEGF CGGTILSEFY ILTAAHCLYQ 240

AKRFKVRVGD RNTEQEEGGE AVHEVEVVIK HNRFTKETYD FDIAVLRLKT PITFRMNVAP 300

ACLPERDWAE STLMTQKTGI VSGFGRTHEK GRQSTRLKML EVPYVDRNSC KLSSSFIITQ 360

NMFCAGYDTK QEDACQGDSG GPHVTRFKDT YFVTGIVSWG EGCARKGKYG IYTKVTAFLK 420

WIDRSMKTRG LPKAKSHAPE VITSSPLK

Underlined: activation peptide (aa 143-194).

Bold: "Common minimal epitope" (aa 177-178)

"Common minimal epitope" on FX (shown in bold in SEQ ID NO: 2 above)

SEQ ID NO: 3

LL heavy chain variable domain mAb 00916

SEQ ID NO: 4

QSVEESGGRL VTPGTPLTLT CTVSGFSLSS <u>YAMS</u>WVRQAP GKGLEWIG<u>II STSGSTFYAT</u> 60

<u>WAKG</u>RFTISK TSTTVDLKII SPTIEDTATY FCAR<u>DMWAGS RYDFNI</u>WGPG TLVTVSS 117 light chain variable domain mAb 00916

SEQ ID NO: 5

ADIVMTQTPA SVEAAVGGTV TIKC<u>QASQSI SSYLA</u>WYQQK PGQRPKLLIY <u>RASTLES</u>GVP 60

SRFKGSGSGT QFTLTISDLE CADAATYYCQ <u>TYYYSGGGSY ASA</u>FGGGTEV VVK 113

-continued heavy chain variable domain mAb 13F62

SEQ ID NO: 6

EVQLVESGGG QVKPGGSLRL SCAASGFTFS TSSIYWVRQA PGKGLEWVSS ISSGSSYIFY 60

ADSVKGRFTI SRDNAKNSLF LQMNSLRAED TAVYYCVSGY SRLLDYWGQG TLVTVSS 117 light chain variable domain mAb 13F62

SEQ ID NO: 7

DVVMTQSPLS LPVTLGQPAS ISCRSSQSLV YSDGNTYLNW FQQRPGQSPR RLIYKVSNRD 60

SGVPDRFSGS GSGTDFTLKI SRVEAEDVGF YYCMQGTHWP LTFGGGTKVE IK 112

Nb 701609

SEQ ID NO: 8

EVQLVESGGGVVQPGGSLRLSCAASGRTFSTYAMGWFRQAPGKEREFVAAISWSGSRTYYADSVKGRFTI

SRDNSKNTVYLQMNSLRPEDTALYYCAADATPANGELDYWGQGTLVTVSS

Nb 701C06

SEQ ID NO: 9

EVQLVESGGGVVQPGGSLRLSCAASGRTFSTYAMGWFRQAPGKEREFVAAISRRGGRTYYADSVKGRFTI

SRDNSKNTVYLQMNSLRPEDTALYYCAADATARDGLLDYWGQGTLVTVSS

Nb 702012

SEQ ID NO: 10

EVQLVESGGGVVQPGGSLRLSCVASGRTFSRYAMGWFRQAPGKEREFVAAISRRGGSTNYADSVKGRFTI

SRDNSKNTVYLQMNSLRPEDTALYYCAADYSSGDGYLDYWGQGTLVTVSS

Nb 701D07

SEQ ID NO: 11

EVQLVESGGGVVQPGGSLRLSCAASGGTLSRYAMGWFRQAPGKEREFVAAITRRGSRTYYADSVKGRFTI

SRDNSKNTVYLQMNSLRPEDTALYYCAADLAPGDYALDYWGQGTLVTVSS

Nb 501A02

SEQ ID NO: 12

EVQLVESGGGLVQPGGSLRLSCAASGFTFSNYEMSWVRQAPGKGLEWVSDIGSGGGVSTYYADSVKGRFT

ISRDNAKNTLYLQMNSLKPEDTAMYYCARGWTYGSDGMDYWGKGTLVTVSS

SEQ ID NOs 13-53 correspond to the sequences recited in table 5 of Example 5.

Nb 721E08

SEQ ID NO: 54

EVQLVESGGGVVQPGGSLRLSCAASGRTFSTYSMGWFRQAPGKEREFVAAITRRGSRTYYADSVKGRFTI

SRDNSKNTVYLQMNSLRPEDTALYYCAADRRPADSYLDYWGQGTLVTVSS

Nb 729A04

SEQ ID NO: 55

EVQLVESGGGVVQPGGSLRLSCAASGFTFSDYAMSWVRQAPGKGLEWVSGITSGGGRTYYADSVKGRFTI

SRDNSKNTLYLQMNSLRPEDTALYYCAAVRTLGLRGSYDYWGQGTLVTVSS

Nb 729008

SEQ ID NO: 56

EVQLVESGGGVVQPGGSLRLSCAASGFTFSDYAMSWVRQAPGKGLEWVSGITGGGRTYYADSVKGRFTIS

RDNSKNTLYLQMNSLRPEDTALYYCAAAILTRTRRTYDYWGQGTLVTVSS

Nb 730003

SEQ ID NO: 57

EVQLVESGGGVVQPGGSLRLSCVASGFTFSDYAMSWVRQAPGKGLEWVSGITSGSGRTYYADSVKGRFTI

SRDNSKNTVYLQMNSLRPEDTALYYCAAAILRGYRKTYDYWGQGTLVTVSS

The underlined sequences represent the CDRs of the mAbs using Kabat numbering and definition whereas the CDRs of Nanobodies® (Nbs) are determined using Kabat numbering and AbM definition as described in Kontermann and Dübel (2010, Eds., Antibody Engineering, vol 2, Springer Verlag Heidelberg Berlin, Martin, Chapter 3, pp. 33-51).

DESCRIPTION

FIX is a vitamin K-dependent coagulation factor with structural similarities to Factor VII, prothrombin, FX, and Protein C. The circulating zymogen form consists of 415 amino acids divided into four distinct domains comprising an N-terminal γ-carboxyglutamic acid-rich (Gla) domain, two EGF domains and a C-terminal trypsin-like serine protease domain. FIX circulates in plasma as a single-chain zymogen (SEQ ID NO:1). Activation of FIX occurs by limited proteolysis at Arg145 and Arg180 to release the activation peptide (residues 146 to 180 of SEQ ID NO:1). Thus, activated FIX (FIXa) is composed of residues 1-145 of SEQ ID NO:1 (light chain) and residues 181-415 of SEQ ID NO:1 (heavy chain).

FIXa is a trypsin-like serine protease that serves a key role in haemostasis by generating, as part of the tenase complex, most of the FXa required to support proper thrombin formation during coagulation.

FX is a vitamin K-dependent coagulation factor with structural similarities to Factor VII, prothrombin, FIX, and protein C. It is synthesised with a pre-pro-sequence containing a hydrophobic signal sequence that targets the protein for secretion. The pro-peptide is important for directing γ-carboxylation to the light chain of FX. Human FX zymogen comprises four distinct domains comprising an N-terminal gamma-carboxyglutamic acid rich (Gla) domain, two EGF domains; EGF1 (residues 46-82) and EGF2 (residues 85-125), respectively, and a C-terminal trypsin-like serine protease domain (residues 195-448). FX circulates in plasma as a two-chain zymogen including residues 1-139 of SEQ ID NO:2 (light chain) and residues 143-448 of SEQ ID NO:2 (heavy chain). Activation of FX occurs by limited proteolysis at Arg194, which results in the release of the activation peptide (residues 143-194). Thus, activated FX (FXa) is composed of residues 1-139 of SEQ ID NO:2 (light chain) and residues 195-448 of SEQ ID NO:2 (activated heavy chain).

The term "binder" as used herein is to be understood in its broadest sense and comprises, for example, lectins, proteins, polypeptides and peptides and all FX-binding molecules or substances. A FX binding molecule comprises, for example, antibodies and antigen-binding fragments thereof (such as—but not limited to—single variable domain antibodies, Nanobodies®, Fabs, Fab'$_2$, Fvs and scFvs), affibodies, adnectins, anticalins, DARPins, avimers. The term "antibody" as used herein refers to a protein, derived from an immunoglobulin sequence, which is capable of binding to an antigen or a portion thereof. The term antibody includes, but is not limited to, full-length antibodies of any class (or isotype), that is, IgA, IgD, IgE, IgG, IgM and/or IgY. An antibody that specifically binds to an antigen, or a fragment thereof, may bind exclusively to that antigen, or a portion or fragment thereof, or it may bind to a limited number of homologous antigens. Usually the simple term "binding" or "binding to" is used and it is generally understood that the binding of an antibody or fragment thereof is a "specific" binding. If the epitope is shared between homologous antigens, it is logical that an antibody may bind further such highly homologous antigens. The term antibody includes antibodies that are multivalent, e.g. bivalent such as bispecific antibodies.

Natural full-length antibodies comprise at least four polypeptide chains: two heavy chains (HC) and two light chains (LC) that are connected by disulfide bonds. In some cases, natural antibodies comprise less than four chains, as in the case of the IgNARs found in Chondrichthyes. One class of immunoglobulins of particular pharmaceutical interest is the IgGs. In humans, the IgG class may be divided into four sub-classes IgG1, IgG2, IgG3 and IgG4, based on the sequence of their heavy chain constant regions. The light chains can be divided into two types, kappa and lambda chains based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable domain ($V_H$) and up to three heavy chain constant ($C_H$) domains: $C_H1$, $C_H2$ and $C_H3$. A light chain may comprise a light chain variable domain ($V_L$) and a light chain constant domain ($C_L$). $V_H$ and $V_L$ domains can be further subdivided into regions of hypervariability, termed complementarity determining regions (CDRs) or hypervariable regions (HvRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the immunoglobulin to host tissues or factors, including, but not limited to various cells of the immune system (effector cells), Fc receptors and the first component, C1q, of the C1 complex of the classical complement system.

Antibodies of the invention may be monoclonal antibodies (mAbs), in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in vitro translation. Antibodies or fragments thereof may also be recombinantly expressed as cell surface bound molecules, by means of e.g. phage display, bacterial display, yeast display, mammalian cell display or ribosome or mRNA display. Antibodies of the current invention may be isolated. The term "isolated antibody" refers to an antibody that has been separated and/or recovered from (an)other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain(s) the ability to bind to or recognise an antigen, such as FX or another target molecule, as described herein. Examples of antigen-binding fragments include (but is not limited to)

Fab, Fab', $Fab_2$, $Fab'_2$, Fv (typically the combination of $V_L$ and $V_H$ domains of a single arm of an antibody), single-chain Fv (scFv); see e.g. Bird et al. Science 1988; 242:423-426; and Huston et al. PNAS 1988; 85:5879-5883), dsFv, Fd (typically the $V_H$ and $C_H1$ domain), monovalent molecules comprising a single $V_H$ and a single $V_L$ chain; minibodies, diabodies, triabodies, tetrabodies, and kappa bodies (see, e.g. Ill et al (1997) Protein Eng 10: 949-57); as well as one or more isolated CDRs or a functional paratope, where the isolated CDRs or antigen-binding residues or polypeptides can be associated or linked together so as to form a functional antibody fragment. These antibody fragments may be obtained using conventional techniques known to those of skill in the art, and the fragments may be screened for utility in the same manner as intact antibodies.

"Fab fragments" of an antibody, including "Fab" and "$Fab'_2$" fragments, can be derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and $C_H1$ domain of the heavy chain. "$Fab'_2$" fragments comprise a pair of "Fab" fragments that are generally covalently linked by their hinge cysteines. A Fab' is formally derived from a $Fab'_2$ fragment by cleavage of the hinge disulfide bonds connecting the heavy chains in the $Fab'_2$. Other chemical couplings than disulfide linkages of antibody fragments are also known in the art. A Fab fragment retains the ability of the parent antibody to bind to its antigen, potentially with a lower affinity. $Fab'_2$ fragments are capable of divalent binding, whereas Fab and Fab' fragments can bind monovalently. Generally, Fab fragments lack the constant $C_H2$ and $C_H3$ domains, i.e. the Fc part, where interaction with the Fc receptors and C1q would occur. Thus, Fab fragments are in general devoid of effector functions. Fab fragments may be produced by methods known in the art, either by enzymatic cleavage of an antibody, e.g. using papain to obtain the Fab or pepsin to obtain the $Fab'_2$, Fab fragments including Fab, Fab', $Fab'_2$ may be produced recombinantly using techniques that are well known to the person skilled in the art. A "Fv" (fragment variable) fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the $V_H$-$V_L$ dimer. Collectively, the six hypervariable regions or a subset thereof confer antigen binding specificity to the antibody.

"Single-chain Fv" or "scFv" antibody comprise the $V_H$ and $V_L$ domains of antibody, where these domains are present in a single polypeptide chain. Generally, the Fv polypeptide further comprises a polypeptide linker between the $V_H$ and $V_L$ domains that enables the scFv to form the desired structure for antigen binding. For a review of scFv, see Pluckthun, 1994, In: *The Pharmacology of Monoclonal Antibodies*, Vol. 113, Rosenburg and Moore eds. Springer-Verlag, New York, pp. 269-315.

"Single-chain Fab" or "scFab" antibody comprise the $V_H$, $C_H1$, $V_L$ and $C_L$ domains of antibody, where these domains are present in a single polypeptide chain. Generally, the Fab polypeptide further comprises a polypeptide linker between either $V_H$ and $C_L$ or $V_L$ and $C_H1$ domains that enables the scFab to form the desired structure for antigen binding (Koerber et al. (2015) J Mol Biol. 427:576-86).

The term "diabodies" refers to small antibody fragments with two antigen-binding sites, in which fragments comprise a heavy chain variable domain ($V_H$) connected to a light chain variable domain ($V_L$) in the same polypeptide chain ($V_H$ and $V_L$). By using a linker that is too short to allow pairing between the two variable domains on the same chain, the variable domains are forced to pair with complementary domains of another chain, creating two antigen-binding sites. The expression "linear antibodies" refers to antibodies as described in Zapata et al. (1995) Protein Eng. 8: 1057-1062. Briefly, these antibodies contain a pair of tandem Fd segments ($V_H$-$C_H1$-$V_H$-$C_H1$) that, together with complementary light chain polypeptides, form a pair of antigen binding regions. Linear antibodies can be bi-specific or monospecific.

Antibody fragments may be obtained using conventional recombinant or protein engineering techniques and the fragments can be screened for binding to an antigen, such as FX in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the antibody, or a variant of any one of the antibodies disclosed herein. An antibody of the invention may be, or may comprise, an antigen-binding portion of one of these antibodies, or variants thereof. For example, an antibody of the invention may be a Fab fragment of one of these antibodies or variants thereof, or it may be a single chain antibody derived from one of these antibodies, or a variant thereof. Also, an antibody of the invention may be a combination of a full length antibody and fragment thereof.

However, even a single variable domain comprising only three hypervariable regions specific for an antigen can retain the ability to recognize and bind antigen with high affinity, although usually at a lower affinity than the entire binding site (Cai & Garen (1996) PNAS 93: 6280-6285). Naturally occurring camelid antibodies that only have a heavy chain variable domain ($V_HH$) can bind antigen (Desmyter et al. (2002) J. Biol. Chem. 277: 23645-23650; Bond et al. (2003) J. Mol. Biol. 332: 643-655). Likewise IgNAR (or $V_{NAR}$), from Cartilaginous fishes provides a single domain antibody binding region. An alternative is provided by Creative Biolabs which uses human tenth fibronectin FN3 domain (10FN3 domain) as scaffold. Such antibody molecules are referred to as single variable domains, immunoglobulin single variable domains or single variable domain fragments. The molecules are monomeric and typically 12-15 kDa in size.

In particular, an immunoglobulin single variable domain or single variable domain may be a Nanobody® (as defined herein) or a suitable fragment thereof. For a general description of Nanobodies®, reference is made to such as WO2008/020079 (page 16).

The term "immunoglobulin single variable domain", interchangeably used with "single variable domain", defines molecules wherein the antigen-binding site is present on, and formed by, a single immunoglobulin domain. This sets immunoglobulin single variable domains apart from "conventional" immunoglobulins or their fragments (such as Fabs, scFvs, etc.), wherein as described above two immunoglobulin domains, in particular two variable domains (a heavy chain variable domain ($V_H$) and a light chain variable domain ($V_L$)) interact to form an antigen-binding site. In contrast, the binding site of an immunoglobulin single variable domain is formed by a single $V_H$ or $V_L$ domain.

Hence, the antigen-binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen-binding site. However, these terms do comprise fragments of conventional immunoglobulins wherein the antigen-binding site is formed by a single variable domain.

Generally, single variable domains will be polypeptide sequences essentially consisting of 4 framework regions (FR1 to FR4 respectively) and 3 complementarity determining regions (CDR1 to CDR3 respectively); or any suitable fragment of such an polypeptide sequence (which will then usually contain at least some of the amino acid residues that form at least one of the CDR's). The amino acid sequence and structure of an immunoglobulin sequence, in particular an immunoglobulin single variable domain such as a Nanobody® can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total length of an immunoglobulin single variable domain is usually, such as for a Nanobody® in the region of 110-120 amino acid residues, is preferably 112-115, and is most preferably 113 amino residues.

Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_HH$ sequence) or a suitable fragment thereof; as long as it is capable of forming a single antigen-binding unit (i.e. a functional antigen-binding unit that essentially consists of the single variable domain, such that the single antigen-binding domain does not need to interact with another variable domain to form a functional antigen-binding unit, as is for example the case for the variable domains that are present in for example conventional antibodies and scFv fragments that need to interact with another variable domain—e.g. through a $V_H/V_L$ interaction—to form a functional antigen-binding domain).

In one embodiment of the invention, the immunoglobulin single variable domains are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain (or an amino acid sequence that is suitable for use as an immunoglobulin single variable domain) may be referred to as a (single) domain antibody; a "dAb" or "sdAb" or a Nanobody® (including but not limited to a $V_HH$, a humanized $V_HH$ or a camelized $V_H$ domain); other single variable domains, or any suitable fragment of any one thereof. For a general description of (single) domain antibodies, reference is also made to such as EP0368684. For the term "dAb", reference is made to for example Ward et al. 1989 (Nature 341: 544), to Holt et al. 2003 (Trends Biotechnol. 21: 484); as well as for example WO2004/068820, WO2006/030220, WO2006/003388 and other published patent applications of Domantis Ltd.

Thus, in the meaning of the present invention, the term "immunoglobulin single variable domain" or "single variable domain" comprises polypeptides which are derived from a non-human source, preferably a camelid, preferably a camelid heavy chain antibody (e.g. $V_HHs$). They may be humanized (e.g. humanized $V_HHs$). Moreover, the term comprises polypeptides derived from non-camelid sources, e.g. mouse or human, which have been "camelized" (e.g. camelized $V_H$ domains), as e.g. described in Davies and Riechmann 1994 (FEBS 339: 285), 1995 (Biotechonol. 13: 475) and 1996 (Prot. Eng. 9: 531) and Riechmann and Muyldermans 1999 (J. Immunol. Methods 231: 25).

The term "mono-specific" antibody, as used herein, refers to an antibody which is capable of binding to one particular epitope (including but not limited to bivalent antibodies).

The term "bi-specific" antibody, as used herein, refers to an antibody which is capable of binding to two different antigens or two different epitopes on the same antigen.

The term "tri-specific" antibody, as used herein, refers to an antibody which is capable of binding to three different antigens or three different epitopes on the same antigen or three different epitopes present on two different antigens.

The term "multi-specific" antibody, as used herein, refers to an antibody which is capable of binding to two or more different antigens or two or more different epitopes on the same antigen. Multispecific antibodies thus comprise bi- and tri-specific antibodies.

Bi-specific antibodies in full length IgG format can be generated by fusion of two individual hybridomas to form a hybrid quadroma which produces a mixture of antibodies including a fraction of bi-specific heterodimerising antibodies (Chelius D. et al.; *MAbs.* 2010 May-June; 2 (3): 309-319). Bi-specific heterodimerising antibodies may alternatively be produced by using recombinant technologies. Heterodimerisation can be also be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bi-specific antibodies are well described in the literature, e.g. (Klein C, et al.; *MAbs.* 2012 November-December; 4 (6): 653-663). Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bi-specifics (e.g. Labrijn et al., *PNAS,* 110, 5145-5150

(2013)). Also the natural Fab-arm exchange method is reported to ensure correct light chains paring.

Multispecific antibody-based molecules may also be expressed recombinantly as fusion proteins combining the natural modules of IgGs to form multi-specific and multi-valent antibody derivatives as described in the literature. Examples of fusion antibodies are DVD-Igs, IgG-scFV, Diabodies, DARTs etc. Specific detection or purification tags, half-life extension moieties or other components can be incorporated in the fusion proteins. Additional non-IgG modalities may also be incorporated in the fusion proteins. Bi-specific full length antibodies based on $F_C$ heterodimerisation are commonly referred to as asymmetric IgGs, irrespective of the LC paring methodology. Generally, bispecific antibodies may be produced in a variety of molecular formats as reviewed by Brinkmann et al. (Brinkmann et al. The making of bispecific antibodies. *Mabs* 9, 182-212 (2017)).

Multi-specific antibody-based molecules may also be produced by chemical conjugation or coupling of individual full length IgGs or coupling of fragments of IgGs to form multi-specific and multivalent antibody derivatives as described in the literature. Examples of fusion antibodies are chemical coupled $Fab'_2$, IgG-dimer etc. Specific detection or purification tags, half-life extension molecules or other components can be incorporated in the conjugate proteins. Additional non-IgG polypeptide may also be incorporated in the fusion proteins. Multi-specific molecules may also be produced by combining recombinant and chemical methods including those described above.

Anti-FX antibodies or antigen-binding fragments thereof as disclosed herein can be used as part of a multispecific procoagulant antibody. Thus, one aspect the invention relates to individual component (intermediate) anti-FX antibodies or antigen-binding fragments thereof that are suitable for use in a multispecific procoagulant antibody, such as a bispecific procoagulant antibody. In one aspect such a bispecific (or multispecific) antibody is capable of binding to FIX and/or the activated form thereof FIXa, and FX.

In one aspect, an antibody of the invention is a chimeric antibody, a human antibody or a humanised antibody. Such antibody can be generated by using, for example, suitable antibody display or immunization platforms or other suitable platforms or methods known in the field). The term "human antibody", as used herein, is intended to include antibodies having variable domains in which at least a portion of a framework region and/or at least a portion of a CDR are derived from human germline immunoglobulin sequences. (For example, a human antibody may have variable domains in which both the framework and CDRs are derived from human germline immunoglobulin sequences.) Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

In one aspect, such a human antibody is a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of a human antibody, such as a conjugate of the antibody and another compound or antibody.

The term "humanised antibody", as used herein, refers to a human/non-human chimeric antibody that contains a sequence (CDRs or parts thereof) derived from a non-human immunoglobulin. A humanised antibody is, thus, a human immunoglobulin (recipient antibody) in which at least residues from a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domains may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDRs from the donor antibody can be transferred by CDR grafting. The CDR grafted humanised antibody can be further optimised for e.g. affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, site-directed mutagenesis, or affinity maturation, etc.

In further aspects, a humanised antibody comprises residues that are not found in the recipient antibody or in the donor antibody. These modifications are made to further refine antibody performance. In general, a humanised antibody comprises at least one—typically two—variable domains, in which all or substantially all of the CDRs correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin. The term "humanised antibody derivative" refers to any modified form of the humanised antibody, such as a conjugate of the antibody and a chemical compound or a conjugate of the antibody with another antibody.

The term "chimeric antibody", as used herein, refers to an antibody comprising portions of antibodies derived from two or more species. For example, the genes encoding such antibody comprise genes encoding variable domains and genes encoding constant regions which originates from two different species. For example, the genes encoding variable segments of a mouse monoclonal antibody may be joined to the genes encoding the constant regions of an antibody of human origin.

The fragment crystallisable region ("Fc region"/"Fc domain") of an antibody is the C-terminal region of an antibody, which comprises the hinge and the constant $C_H2$ and $C_H3$ domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc-gamma receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of $C_H1$ is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into two monovalent $V_H$-$V_L$ fragments. For example, in an IgG4 constant region, residue S228 (according to the EU numbering index and S241 according to Kabat) may be mutated to a proline (P) residue to stabilise inter heavy chain disulphide bridge formation at the hinge (see, e.g., Angal et al. Mol Immunol. 1993; 30:105-8).

Antibodies or fragments thereof may be defined in terms of their complementarity-determining regions (CDRs). The term "complementarity-determining region" or "hypervariable region", when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. 1991; Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917). Typically, the numbering of amino acid residues in this region is performed by the method described in Kabat et al. supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The amino acid residues of a $V_HH$ domain may be numbered according to the general numbering for $V_H$ domains given by Kabat et al. as applied to $V_HH$ domains from Camelids, as shown e.g., in FIG. 2 of Riechmann and Muyldermans (1999, J. Immunol. Methods 231: 25-38). Alternative methods for numbering the amino acid residues of VH domains, which methods can also be applied in an analogous manner to $V_HH$ domains, are known in the art.

Determination of CDRs may also be done according to different methods. In the CDR determination according to Kabat, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113.

In the present document, CDR sequences of single variable domain antibodies (Nanobodies®) are determined using the AbM definition according to Kontermann and Dübel (2010, Eds., Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

In the present document, CDR sequences of IgG antibodies (including full-length IgG antibodies and Fab fragments thereof) are determined using the Kabat definition according to Kontermann and Dübel (2010, Eds., Antibody Engineering, vol 2, Springer Verlag Heidelberg Berlin, Martin, Chapter 3, pp. 33-51). According to this method, the CDRs of the light chain variable domain is defined as position 24-34 (CDR1), position 50-56 (CDR2) and position 89-97

(CDR3), while the CDRs of the heavy chain variable domain is defined as position 31-35 (CDR1), position 50-65 (CDR2) and position 95-102 (CDR3).

The term "framework region" or "FR" residues refer to those $V_H$ or $V_L$ amino acid residues that are not within the CDRs, as defined herein.

In one embodiment an antibody or antigen-binding fragment thereof of the invention may comprise a CDR from one or more of the specific antibodies disclosed herein.

The term "procoagulant antibody" refers to an antibody which potentiates blood coagulation for example by accelerating the process of blood coagulation and/or increasing the enzymatic activity of one or more coagulation factors.

The term "procoagulant activity" refers to the ability of a compound, such as an antibody, to potentiate blood coagulation for example by accelerating the process of blood coagulation and/or increasing the enzymatic activity of one or more coagulation factors.

It should be noted that—as is well known in the art for $V_H$ domains and for $V_H$H domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a $V_H$ domain and a $V_H$H domain will usually be in the range of from 110 to 120, often between 112 and 115. It should however be noted that smaller and longer sequences may also be suitable for the purposes described herein. An antibody of the invention may comprise a CDR from one or more of the specific antibodies disclosed herein.

The term "antigen" (Ag) refers to the molecular entity used for immunisation of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunisation process, or other process, e.g. phage display, used for generating the Ab.

The term "epitope", as used herein, is defined in the context of a molecular interaction between an "antigen-binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined using various criteria (e.g. a distance cut-off of 2-6 Å, such as 3 Å, such as 3.5 Å such as 4 Å, such as 4.5 Å, such as 5 Å; or solvent accessibility) for atoms in the Ab and Ag molecules.

FX/FXa may comprise a number of different epitopes, which may include, without limitation, (1) linear peptide epitopes (2) conformational epitopes which consist of one or more non-contiguous amino acids located near each other in the mature FX/FXa conformation; and (3) epitopes which consist, either in whole or part, of molecular structures covalently attached to FX/FXa, such as carbohydrate groups.

The epitope for a given antibody (Ab)/antigen (Ag) pair can be described and characterized at different levels of detail using a variety of experimental and computational epitope mapping methods. The experimental methods include mutagenesis, X-ray crystallography, Nuclear Magnetic Resonance (NMR) spectroscopy, Hydrogen Deuterium eXchange Mass Spectrometry (HDX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

The epitope and paratope for a given antibody (Ab)/antigen (Ag) pair may be identified by routine methods. For example, the general location of an epitope may be determined by assessing the ability of an antibody to bind to different fragments or variants of FX. The specific amino acids within FX that make contact with an antibody (epitope) and the specific amino acids in an antibody that make contact with FX (paratope) may also be determined using routine methods. An antibody according to the current invention may be able to compete with another molecule, such as a naturally occurring ligand or receptor or another antibody, for binding to FX.

A competitive binding assay can be conducted in which the binding of the antibody to the target is compared to the binding of the target by another ligand of that target, such as another antibody.

Antibodies that bind to the same antigen can be characterised with respect to their ability to bind to their common antigen simultaneously and may be subject to "competition binding"/"binning". In the present context, the term "binning" refers to a method of grouping antibodies that bind to the same antigen. "Binning" of antibodies may be based on competition binding of two antibodies to their common antigen in assays based on standard techniques.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are considered "competing antibodies". If a second antibody is capable of binding to an antigen at the same time as the reference antibody, the second antibody is said to belong to a separate "bin". In this case, the reference and the second antibody do not competitively bind the same part of an antigen and are considered "non-competing antibodies".

Antibody "binning" does not provide direct information about the epitope.

Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes. Thus, in some embodiments antibodies of the invention will bind to the same epitope as at least one of the antibodies specifically disclosed herein.

Competition assays for determining whether an antibody binds to the same epitope as, or competes for binding with, an anti-FX antibody disclosed herein are known in the art. Exemplary competition assays include immunoassays (e.g., ELISA assays, RIA assays), Surface Plasmon Resonance analysis (e.g., using a BIAcore™ instrument), biolayer interferometry and flow cytometry. Typically, a competition assay involves the use of an antigen bound to a solid surface or expressed on a cell surface, a test FX binding antibody and a reference antibody. The reference antibody is labelled and the test antibody is unlabelled. Competitive inhibition is measured by determining the amount of labelled reference antibody bound to the solid surface or cells in the presence of the test antibody. Usually the test antibody is present in excess (e.g. 1, 5, 10, 20, 100, 1000, 10000 or 100000-fold) of the reference antibody. Antibodies identified as being competitive in the competition assay (i.e., competing antibodies) include antibodies binding to the same epitope, or overlapping epitopes, as the reference antibody, and antibodies binding to an adjacent epitope sufficiently proximal to the epitope bound by the reference antibody for steric hindrance to occur.

In an exemplary competition assay, a reference anti-FX or anti-FXa antibody is biotinylated using commercially available reagents. The biotinylated reference antibody is mixed with serial dilutions of the test antibody or unlabelled reference antibody (self-competition control) resulting in a mixture of various molar ratios (e.g. 1, 5, 10, 20, 100, 1000, 10000 or 100000-fold) of test antibody (or unlabelled reference antibody) to labelled reference antibody. The antibody mixture is added to a FX or FXa polypeptide coated-ELISA plate. The plate is then washed, and horseradish peroxidase (HRP)-strepavidin is added to the plate as the detection reagent. The amount of labelled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a Spectrometer (e.g. a SpectraMax® M2 spectrometer (Molecular Devices)). The response (OD units) corresponding to zero percent inhibition is determined from wells without any competing antibody. The response (OD units) corresponding to 100% inhibition, i.e. the assay background is determined from wells without any labelled reference antibody or test antibody. Percent inhibition of labelled reference antibody to FX or FXa by the test antibody (or the unlabelled reference antibody) at each concentration is calculated as follows: % inhibition=(1−(OD units−100% inhibition)/(0% inhibition−100% inhibition))*100.

A person skilled in the art understands that similar assays may be performed to determine if two or more anti-FX/FXa antibodies share a binding region, a bin and/or competitively bind the antigen. A person skilled in the art also appreciates that the competition assay can be performed by using various detection systems known in the art.

A test antibody competes with a reference antibody for binding to the antigen if an excess of one antibody (e.g., 1, 5, 10, 20, 100, 1000, 10000 or 100000-fold) inhibits binding of the other antibody, e.g., by at least 50%, 75%, 90%, 95% or 99%, as measured in a competitive binding assay. An example of a competition assay is provided in the method section 5.

The term "binding affinity" is herein used as a measure of the strength of a non-covalent interaction between two molecules, e.g. an antibody, or fragment thereof, and an antigen. The term "binding affinity" is used to describe monovalent interactions.

Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

The value of the dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR. An example of an SPR binding assay is provided in Example 2 herein.

A FX binder, such as an antibody or a fragment thereof according to the invention may have a $K_D$ for its target of $1\times10^{-4}$M or less, $1\times10^{-5}$M or less, $1\times10^{-6}$M or less, $1\times10^{-7}$M or less, $1\times10^{-8}$M or less, or $1\times10^{-9}$M or less, or $1\times10^{-10}$M or less, $1\times10^{-11}$M or less, $1\times10^{-12}$M or less, $1\times10^{-13}$M or less or $1\times10^{-14}$M or less. In an embodiment the $K_D$ of an antibody according to the invention may be less than 100 μM such as less than 50 μM, such as less than 10 μM. In one embodiment the $K_D$ is less than 9 μM, such as less than 8 μM, such as less than 7 μM, such as less than 6 μM, such as less than 5 μM. In one embodiment the $K_D$ is less than 4 μM, such as less than 3 μM, such as less than 2 μM, such as less than 1 μM.

Identity

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods.

In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

Pharmaceutical Formulations

In another aspect, the present invention provides compositions and formulations comprising compounds of the invention, such as the antibodies described herein. For example, the invention provides a pharmaceutical composition that comprises antibodies or antigen-binding fragment thereof of the invention, formulated together with a pharmaceutically acceptable carrier.

Accordingly, one object of the invention is to provide a pharmaceutical formulation comprising such an antibody or antigen-binding fragment thereof which is present in a concentration from 0.1 mg/ml to 500 mg/ml, and wherein said formulation has a pH from 2.0 to 10.0. The formulation may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension, but may also include colloids, dispersions, emulsions, and multi-phase materials. The term “aqueous formulation” is defined as a formulation comprising at least 50% w/w water. Likewise, the term “aqueous solution” is defined as a solution comprising at least 50% w/w water, and the term “aqueous suspension” is defined as a suspension comprising at least 50% w/w water.

In another embodiment, the pharmaceutical formulation is a freeze-dried formulation, to which a solvent and/or a diluent is added prior to use.

In a further aspect, the pharmaceutical formulation comprises an aqueous solution of such an antibody, and a buffer, wherein the antibody is present in a concentration from 0.1 mg/ml or above, and wherein said formulation has a pH from about 2.0 to about 10.0.

In one embodiment, the present invention relates to an injection device with content of said composition. In some embodiments, the pharmaceutical composition of the invention is intended for use and/or contained in an injection device. In some embodiments, the injection device is a disposable, pre-filled, multi-dose pen of the FlexTouch® type (supplier Novo Nordisk A/S, Denmark). In some embodiments the injection device is a single shot device.

In some embodiments the injection device is a fixed dose device, such as one configured to deliver multiple predetermined doses of drug, sometimes referred to as a multiple fixed dose device or a fixed dose, multi-shot device.

Administration

A compound of the invention, such as an antibody or antigen-binding fragment thereof, or compositions comprising such compound, may be administered parenterally, such as intravenously, such as intramuscularly, such as subcutaneously. Alternatively, a compound of the invention, such as an antibody or antigen-binding fragment thereof, or compositions comprising such compound, may be administered via a non-parenteral route, such as periorally or topically. The compound or composition may be administered prophylactically. Alternatively, the compound or composition may be administered therapeutically (on demand).

Dosages

The dose of the compounds to be delivered may be from about 0.01 mg to 500 mg of the compound per day, preferably from about 0.1 mg to 250 mg per day, and more preferably from about 0.5 mg to about 250 mg per day, per week, per second week or per month as loading and maintenance doses, depending on the severity of the condition. A suitable dose may also be adjusted for a particular compound based on the properties of that compound, including its in vivo half-life or mean residence time and its biological activity. For example, compounds to be delivered could in one embodiment be administered once weekly, or in another embodiment once every second week or in another embodiment one monthly and in either of said embodiments in a dose of for example 0.1, 0.25, 0.5, 1, 1.5, 2, 2.5, 3, 3.5, 4, 4.5, 5, 5.5, 6, 6.5, 7, 7.5, 8, 8.5, 9, 9.5 or 10 mg per kg body weight.

Compositions containing the compounds as disclosed herein can be administered for prophylactic and/or in some embodiments therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as “therapeutically effective amount”. As will be understood by the person skilled in the art amounts effective for this purpose will depend on the severity of the disease or injury as well as the weight and general state of the subject.

In one aspect, the invention relates to FX binding molecules with the capability of stimulating the activation of FX to generate FXa. As described above, such functionality is desirable in the quest for new and improved treatment to improve the coagulation function in particular haemophilia patients.

In one embodiment, the invention relates to a FX binder, such as an antibody or antigen-binding fragment thereof which binds human FX and stimulates FX activation.

In one embodiment, the invention relates to a FX binder, such as an antibody or antigen-binding fragment thereof, wherein the FX binder, antibody or antigen-binding fragment thereof is binding human FX and capable of stimulating FX activation.

It is of special interest that the activation observed occurs also in the absence of a FIX binding moiety, such as FVIII or a FVIII mimetic compound comprising a FIXa binder which can bring FX and FIXa together. In one embodiment, the FX binder, such as an antibody or antigen-binding fragment thereof binds human FX and thereby stimulates proteolysis of FX by FIXa generating FXa.

In one embodiment the antibody or antigen-binding fragment thereof stimulates FXa generation independently of the presence of a FIXa binding moiety. In one embodiment the antibody or antigen-binding fragment thereof is capable of stimulating FXa generation independently of the presence of a FIXa binding moiety.

In one embodiment, the FX binder, such as an antibody or antigen-binding fragment thereof capable of binding FX, is capable of making FX more prone to proteolysis independently of the presence of a FIXa binding moiety. In one embodiment, the FX binder, such as an antibody or antigen-binding fragment thereof capable of binding FX, is capable of making FX more prone to proteolysis by FIXa. In one embodiment, the FX binder, such as an antibody or antigen-binding fragment thereof capable of binding FX, is capable of making FX more prone to proteolysis independently of the presence of a FIXa binding moiety.

The ability of a FX binder to stimulate FXa generation may be tested by a suitable assay known to the person skilled in the art. References is made to example 3 herein providing an in vitro assay suitable for testing the activating function of a given FX binder. In one embodiment, the FX binder, such as an antibody or antigen-binding fragment thereof capable of binding FX, stimulates FX activation as determined by Example 3. A FX binder is stimulatory or capable of stimulating FX activation when an increase in FXa is measured in the presence of said FX binder compared to the equivalent assay performed with no FX binder or a non-activating FX binder.

The ability of a FX binder to promote FIXa-mediated FX-activation is considered present when an increase in FX activation rate—as described in the assay according to Example 3 herein—is observed for a given FX binder relative to absence of FX binder, i.e. when a fold increase in FX activation above 1 is observed, such as above 1.1, 1.2, 1.3, 1.4, 1.5, 1.6, 1.7, 1.8 or 1.9. In preferred embodiments the fold increase in FX activation observed is more than 2 fold such as 3, 4, 5, 6, 7, 8, 9, 10, 20, 30, 40, 50, 60, 70, 80, 90 or 100 fold or above. In one embodiment the fold increase in FX activation is 2-100,000 fold. In one such embodiment the fold increase in FX activation is 2-500 fold. In one such embodiment the fold increase in FX activation is 3-500 fold. In another such embodiment the fold increase in FX activation is 4-500 fold. In another such embodiment the increase in FX activation is 5-100 fold. In another embodiment the increase in FX activation is 10-100 fold, such as 10-83 fold.

In order to avoid that the avidity of a FX-binder influences the measurements in an assay such as that described in Example 3 herein, the assay should preferably be performed by using a monovalent FX binder. In case the FX binder is a bi- or multi-valent FX binder, the activation assay should thus be performed using a monovalent antigen-binding fragment thereof.

An aspect of the invention relates to a FX binder, such as an antibody or antigen-binding fragment thereof which binds human FX stronger than FXa. In one embodiment, the FX binder does not bind FXa. In another embodiment, the FX binder preferentially binds FX relative to FXa. In one such embodiment, the FX binder binds FXa with a lower affinity. As FX is distinguished from FXa by the presence of the activation peptide, the invention in an aspect relates to a FX binder such as an antibody or antigen-binding fragment thereof which binds the activation peptide of human FX. The activation peptide of human FX is defined by amino acid residues 143-194 of SEQ ID NO:2.

In one embodiment, the antibody or antigen-binding fragment thereof binds the activation peptide of FX identified by amino acid residues 143-194 of SEQ ID NO:2. In a further embodiment, the antibody or antigen-binding fragment thereof binds amino acid residues 170-185 within the activation peptide of FX as identified by SEQ ID NO:2.

Based on the peptide array performed as described in Example 5, a shared binding site for the identified FX activating FX binders was identified. A common minimal peptide epitope was determined and found to comprise the peptide "LL" within the activation peptide of FX corresponding to amino acid residues 177-178 of human FX as identified by SEQ ID NO:2.

In an embodiment, the invention relates to a FX binder, such as an antibody or antigen-binding fragment thereof, capable of binding "LL" within the activation peptide of FX corresponding to amino acid residues 177-178 of human FX as identified by SEQ ID NO:2.

In an embodiment, the invention relates to a FX binder, such as an antibody or antigen-binding fragment thereof capable of binding the activation peptide of FX, and wherein the common minimal epitope as determined by peptide array, is comprised by "LL" (amino acid residues 177-178 of SEQ ID NO:2).

In an embodiment, the FX binder, such as an antibody or antigen-binding fragment thereof binds the activation peptide of FX identified by amino acid residues 143-194 of SEQ ID NO:2 and wherein the common minimal epitope as determined by peptide array is comprised by "LL" (amino acid residues 177-178 of SEQ ID NO:2).

It is well known in the art that antigen-binding molecules may take various forms. A series of well-known types of molecular formats are described herein, while it is also noted that it is not to be considered an exhaustive list, and that the skilled artisan will be able to apply the teaching of the present application to their preferred molecular format without difficulties.

In one embodiment, the FX binder is a monovalent. In one such embodiment the FX binder is an immunoglobulin single variable domain, such as a (single) domain antibody or antibody fragment thereof or a Nanobody®, a $V_HH$, a humanized $V_HH$ or a camelized $V_H$ domain. In one embodiment the FX binder is Fab. In one embodiment the FX binder is bi-valent. In one embodiment the FX binder is a monoclonal whole antibody (mAb) or an antigen-binding fragment of a mAb.

An aspect of the invention relates to the identification of a FX binder which is capable of stimulating FX activation. In one such embodiment, a method is provided comprising the following steps a) providing a FX binder b) testing the FX binder in an in vitro assay suitable for testing the FX activating function of a given FX binder and c) selecting a FX binder capable of stimulating FX activation.

As mentioned above, a FX binder capable of stimulating FX activation may be a desired element to include in a bi-specific molecule, or tri-specific molecule or even a multi-specific molecule.

An aspect of the invention thus relates to bi-, tri and multi-specific molecules, such as antibody molecules (or antigen-binding fragments thereof) comprising at least one FX binding moiety providing FX stimulation.

An aspect of the invention relates to the use of a molecule, such as an antibody or an antigen-binding fragment thereof as described herein for the manufacture of a medicament.

An aspect of the invention relates a molecule, such as an antibody or an antigen-binding fragment thereof as described herein for use in a method of treatment.

An aspect of the invention relates use of a molecule, such as an antibody or an antigen-binding fragment thereof as described herein for the treatment of a coagulopathy, such as haemophilia.

An aspect of the invention relates to a method of treatment comprising the step of administering to an individual in need thereof, a therapeutically effective dose of a molecule, such as an antibody or an antigen-binding fragment thereof as described herein. In one embodiment the method is for treatment a patient suffering from a coagulopathy, such as haemophilia and in particular haemophilia A with or without inhibitors. In one embodiment the method is for treatment a patient suffering from haemophilia B with or without inhibitors.

EMBODIMENTS

1. An antibody or antigen-binding fragment thereof capable of binding to the activation peptide of FX identified by amino acid residues 143-194 of SEQ ID NO:2.
2. An antibody or antigen-binding fragment thereof capable of binding to one or more of amino acid residues 170-185 within the activation peptide of FX as identified by SEQ ID NO:2.
3. An antibody or antigen-binding fragment thereof capable of binding to "LL" within the activation peptide of FX corresponding to amino acid residues in position 177-178 of human FX as identified by SEQ ID NO:2.
4. An antibody or antigen-binding fragment thereof capable of binding to the activation peptide of FX, wherein the common minimal epitope as determined by peptide array, comprises "LL" (AA 177-178 of SEQ ID NO:2).
5. An antibody or antigen-binding fragment thereof capable of binding FX, wherein the antibody or antigen-binding fragment is capable of stimulating FX activation.

6. An antibody or antigen-binding fragment thereof capable of binding FX, wherein the antibody or antigen-binding fragment is capable of stimulating FX activation by FIXa.
7. An antibody or antigen-binding fragment thereof capable of binding FX, wherein the antibody or antigen-binding fragment is capable of stimulating FX activation by FIXa independently of the presence of a FIXa binder.
8. An antibody or antigen-binding fragment thereof capable of binding FX according to any of embodiments 1-4, wherein the antibody or antigen-binding fragment thereof is capable of stimulating FX activation.
9. The antibody or antigen-binding fragment thereof capable of binding FX according to any of the embodiments 5-8, wherein the capability of the antibody or antigen-binding fragment thereof to stimulate FX activation is determined as described in Example 3 herein.
10. An antibody or antigen-binding fragment thereof capable of binding FX, wherein the antibody or antigen-binding fragment thereof stimulates FX activation by FIXa independently of the presence of a FIXa binding moiety.
11. The antibody or antigen-binding fragment thereof capable of binding FX according to any of the embodiments 5-10, wherein the stimulation of FX activation is determined as described in Example 3 herein.
12. An antibody or antigen-binding fragment thereof capable of binding FX, wherein the antibody or antigen-binding fragment is capable of making FX more prone to activation.
13. An antibody or antigen-binding fragment thereof capable of binding FX, wherein the antibody or antigen-binding fragment is capable of making FX more prone to proteolysis by FIXa.
14. An antibody or antigen-binding fragment thereof capable of binding FX, wherein the antibody or antigen-binding fragment is capable of making FX more prone to proteolysis by FIXa independently on the presence of a FIXa binding moiety.
15. The antibody or antigen-binding fragment thereof capable of binding FX according to any of the embodiments 12-14, wherein the capability of the antibody or antigen-binding fragment to make FX more prone to proteolysis is determined as described in Example 3 herein.
16. The antibody or antigen-binding fragment thereof capable of binding FX according to any of the embodiments 1-4, wherein the antibody or antigen-binding fragment is capable of stimulating FX activation according to any of the embodiments 5-11.
17. The antibody or antigen-binding fragment thereof according to any of the embodiments 1-4, wherein the antibody or antigen-binding fragment thereof is a single variable domain antibody which stimulates FX activation according to any of the embodiments 5-11.
18. The antibody or antigen-binding fragment thereof capable of binding FX according to any of the embodiments 1-4, wherein the antibody or antigen-binding fragment thereof is a single variable domain antibody which is capable of making FX more prone to proteolysis according to any of the embodiments 12-15.
19. The antibody or antigen-binding fragment thereof capable of binding FX according to any of the embodiments 5-18, wherein a monovalent antigen-binding fragment thereof
    a. stimulates FX activation;
    b. stimulates FX activation by FIXa;
    c. is capable of stimulating FX activation;
    d. is capable of stimulating FX activation by FIXa;
    e. is capable of making FX more prone to proteolysis; or
    f. is capable of making FX more prone to proteolysis by FIXa.
20. The antibody or antigen-binding fragment thereof capable of binding FX according to any of the previous embodiments, wherein the antibody or antigen-binding fragment has a binding affinity determined as the equilibrium dissociation constant ($K_D$) is less than 10 μM, such as less than 9 μM, such as less than 8 μM, such as less than 7 μM, such as less than 6 μM, such as less than 5 μM, such as less than 4 μM, such as less than 3 μM or such as less than 2 μM.
21. The antibody or antigen-binding fragment thereof according to any of the previous embodiments, wherein the antibody or antigen-binding fragment is monovalent.
22. The antibody or antigen-binding fragment thereof according to any of the previous embodiments, wherein the antibody or antigen-binding fragment thereof is an immunoglobulin single variable domain or antibody fragment thereof, such as a domain antibody, a Nanobody®, a $V_HH$, a humanized $V_HH$ or a camelized $V_H$ domain.
23. The antibody or antigen-binding fragment thereof according to any of the previous embodiments wherein the antibody or antigen-binding fragment thereof is a Fab, scFab, Fv or scFv.
24. The antibody or antigen-binding fragment thereof according to any of the previous embodiments 1-15, wherein the antibody or antigen-binding fragment thereof is bivalent.
25. The antibody or antigen-binding fragment thereof according to embodiment 24, wherein the antibody or antigen-binding fragment is a mAb of a $Fab'_2$.
26. The antibody or antigen-binding fragment thereof according to any of the previous embodiments wherein the heavy chain variable domain is at least 90, 91, 92, 93, 94, 95, 96, 97, 98 or 99% identical to the sequence identified by SEQ ID NO:8, 9, 10, 11, 54, 55, 56 or 57, respectively.
27. The antibody or antigen-binding fragment thereof according to any of embodiments 1-25, wherein the antibody or antigen-binding fragment thereof comprises
    a. three heavy chain CDR sequences with at most 10 amino acid residue changes compared to the three CDR sequences of the heavy chain variable domain identified by SEQ ID NO:8;
    b. three heavy chain CDR sequences with at most 10 amino acid residue changes compared to the three CDR sequences of the heavy chain variable domain identified by SEQ ID NO:9;
    c. three heavy chain CDR sequences with at most 10 amino acid residue changes compared to the three CDR sequences of the heavy chain variable domain identified by SEQ ID NO:10;
    d. three heavy chain three CDR sequences with at most 10 amino acid residue changes compared to the three CDR sequences of the heavy chain variable domain identified by SEQ ID NO:11;
    e. three heavy chain CDR sequences with at most 10 amino acid residue changes compared to the three CDR sequences of the heavy chain variable domain identified by SEQ ID NO:54;

f. three heavy chain CDR sequences with at most 10 amino acid residue changes compared to the three CDR sequences of the heavy chain variable domain identified by SEQ ID NO:55;

g. three heavy chain CDR sequences with at most 10 amino acid residue changes compared to the three CDR sequences of the heavy chain variable domain identified by SEQ ID NO:56; or three heavy chain CDR sequences with at most 10 amino acid residue changes compared to the three CDR sequences of the heavy chain variable domain identified by SEQ ID NO:57.

28. The antibody or antigen-binding fragment thereof according to embodiment 27, wherein the three heavy chain CDR sequences have at most 9, such as 8, such as 7 or such as 6 amino acid changes compared to the three CDRs of the identified SEQ ID NOs.

29. The antibody or antigen-binding fragment thereof according to embodiment 28, wherein the three heavy chain CDR sequences have at most 5, such as 4, such as 3, such as 2 or at most 1 amino acid changes compared to the three CDRs of the identified SEQ ID NOs.

30. An antibody or antigen-binding fragment thereof comprising or consisting of SEQ ID NO:8, 9, 10, 11, 54, 55, 56, or 57.

31. An antibody or antigen-binding fragment thereof comprising the three CDRs of SEQ ID NO:8, 9, 10, 11, 54, 55, 56, or 57.

32. An antibody or antigen-binding fragment thereof, wherein the antibody or antigen-binding fragment competes with a reference antibody or antigen-binding fragment comprising or consisting of SEQ ID NO:8, 9, 10, 11, 54, 55, 56, or 57.

33. An antibody or antigen-binding fragment thereof comprising the heavy chain variable domain (SEQ ID NO:4) and light chain variable domain (SEQ ID NO:5) of mAb 00916.

34. An antibody or antigen-binding fragment thereof comprising the heavy chain variable domain (SEQ ID NO:6) and light chain variable domain (SEQ ID NO:7) of mAb 13F62.

35. An antibody or antigen-binding fragment thereof comprising the three CDRs of the heavy chain variable domain (SEQ ID NO:4) and the three CDRs of the light chain variable domain (SEQ ID NO:5) of mAb 00916.

36. An antibody or antigen-binding fragment thereof comprising the three CDRs of the heavy chain variable domain (SEQ ID NO:6) and the three CDRs of the light chain variable domain (SEQ ID NO:7) of mAb 13F62.

37. An antibody or antigen-binding fragment thereof, wherein the antibody or antigen-binding fragment competes with a reference antibody or antigen-binding fragment comprising the heavy chain variable domain (SEQ ID NO:4) and light chain variable domain (SEQ ID NO:5) of mAb 00916.

38. An antibody or antigen-binding fragment thereof, wherein the antibody or antigen-binding fragment competes with a reference antibody or antigen-binding fragment comprising the heavy chain variable domain (SEQ ID NO:6) and light chain variable domain (SEQ ID NO:7) of mAb 13F62.

39. The antibody or antigen-binding fragment thereof according to any of the embodiments 26-38 wherein the antibody or antigen-binding fragment is capable of stimulating FX activation according to any of the embodiments 5-9.

40. The antibody or antigen-binding fragment thereof according to any of the embodiments 26-38 wherein the antibody or antigen-binding fragment stimulates FX activation according to any of the embodiments 9-11.

41. The antibody or antigen-binding fragment thereof according to any of the embodiments 26-38 wherein the antibody or antigen-binding fragment is capable of making FX more prone to proteolysis according to any of the embodiments 12-15.

42. A bi-, tri- or multi-specific molecule comprising an antibody or antigen-binding fragment, according to any of the previous embodiments.

43. The bi-, tri- or multi-specific molecule comprising an antibody or antigen-binding fragment thereof, according to any of the previous embodiments, wherein said antibody or antigen-binding fragment thereof is a single variable domain antibody.

44. A pharmaceutical composition comprising the antibody or antigen-binding fragment thereof according to any of the previous embodiments and optionally one or more pharmaceutically acceptable carrier(s).

45. Use of the antibody or antigen-binding fragment thereof or composition according to any of the previous embodiments for the manufacture of a medicament for use in the treatment of a coagulopathy, such as haemophilia A with or without inhibitors, or such as haemophilia B with or without inhibitors.

46. The antibody or antigen-binding fragment thereof or composition according to any of the embodiments 1-44 for use in the treatment of a coagulopathy, such as haemophilia A with or without inhibitors or such as haemophilia B with or without inhibitors.

47. A method of treating a subject suffering from a blood coagulation disorder such as haemophilia, comprising administering to said subject an antibody or antigen-binding fragment thereof or composition according to any of the previous embodiments.

48. A method according to embodiment 47 wherein the coagulopathy or blood coagulation disorder is haemophilia A or B with inhibitors or without inhibitors.

49. A method for identifying an antibody according to any of the embodiments 1-25 comprising the steps of a) providing a FX binder, b) testing the FX binder in an in vitro assay suitable for testing the FX activating function of the FX binder provided in step a and c) selecting a FX binder capable of stimulating FX activation.

50. A method for identifying an antibody according to any of the embodiments 5-23 comprising the steps of a) providing a FX binder, b) testing the FX binder in an in vitro assay suitable for testing the FX activating function of the FX binder provided in step a and c) selecting a FX binder capable of making FX more prone to proteolysis, for example by FIXa.

51. A eukaryotic cell which expresses the antibody or antigen-binding fragment thereof, according to any of the embodiments 1-43.

52. A kit comprising the antibody or antigen-binding fragment thereof or composition according to any of the embodiments 1-44 and instructions for use.

EXAMPLES AND METHODS

General Methods

Preparation of FX-Binding Nanobodies

General Molecular Biology

For general molecular biology techniques, please see Molecular Cloning: A Laboratory Manual (Third Edition, 2001, Sambrook, Fritsch and Maniatis eds., CSHL Press, Cold Spring Harbor, NY).

1. Immunizations and Libraries

After approval of the Ethical Committee of the Ablynx Camelid Facility (LA1400575), one llama and one alpaca were immunized with FX (Haemotologic Technologies, VT USA).

Cloning of heavy chain-only antibody fragment repertoires and preparation of phage immune libraries was performed as follows.

Following the final immunogen injection, blood samples were collected. From these blood samples, peripheral blood mononuclear cells (PBMCs) were prepared using Ficoll-Hypaque according to the manufacturer's instructions (Amersham Biosciences, Piscataway, NJ, US). From the PBMCs, total RNA was extracted and used as starting material for RT-PCR to amplify the $V_H$H/Nanobody®-encoding DNA segments, essentially as described in WO2005/044858. In short, the Nanobody®-encoding DNA segments were cloned into phagemid vector pAX212 enabling production of phage particles displaying Nanobodies® fused with $His_6$- and $FLAG_3$-tags. Subsequently, phages were prepared and stored according to standard protocols.

Synthetic Libraries

Synthetic libraries were generated by cloning synthetic Nanobody® gene fragments into phagemid vector pAX190, which has the same features as the above described pAX212, but with differences in the multiple cloning site.

Library Screening of Nanobodies Binding to FX

Nanobody® Phage Display selections were performed with the generated immune and synthetic libraries. The libraries were subjected to one to four successive rounds of enrichment against different combinations of immobilized human FX (Haemotologic Technologies, VT USA) and cynomolgus FX (Novo Nordisk in house production).

In order to specifically enrich for Nanobodies that were selective for FX versus FXa, in certain experiments excess soluble FXa was used for competition during the incubation of the libraries with the immobilized FX.

In order to specifically enrich for Nanobodies that were selective for FX versus other structurally related coagulation factors, in certain experiments excess soluble FIX was used for competition during the incubation of the libraries with the immobilized FX.

Approximately 4500 individual clones from the selection outputs were screened for binding in ELISA (using periplasmic extracts from *E. coli* cells expressing the Nanobodies) against human and cynomolgus FX, FXa or FIX. Approximately 1500 clones that showed specific binding to human FX/FXa were identified, of which the majority showed cross-binding to cynomolgus FX. Some clones showed preferential binding to FX versus FXa. Sequence analysis of the ELISA positive clones identified approximately 700 unique sequences of Nanobodies binding to FX/FXa.

2. Generation of Nanobody® Expression Constructs

Sequence analysis of Nanobodies from phage display selection outputs was done according to commonly known procedures (Pardon et al. (2014) Nat Protoc 9: 674).

Nanobody®-containing DNA fragments, obtained by PCR with specific combinations of forward FR1 and reverse FR4 primers each carrying a unique restriction site, were digested with the appropriate restriction enzymes and ligated into the matching cloning cassettes of Nanobody® expression vectors (described below). The ligation mixtures were then transformed to electrocompetent *Escherichia coli* TG1 (60502, Lucigen, Middleton, WI) or TOP10 (C404052, ThermoFisher Scientific, Waltham, MA) cells which were then grown under the appropriate antibiotic selection pressure (kanamycin or Zeocin). Resistant clones were verified by Sanger sequencing of plasmid DNA (LGC Genomics, Berlin, Germany).

Monovalent Nanobodies were expressed in *E. coli* TG1 from a plasmid expression vector containing the lac promoter, a resistance gene for kanamycin, an *E. coli* replication origin and a Nanobody® cloning site preceded by the coding sequence for the OmpA signal peptide. In frame with the Nanobody® coding sequence, the vector codes for a C-terminal FLAG3 and HIS6 tag. The signal peptide directs the expressed Nanobodies to the periplasmic compartment of the bacterial host.

Expression and Purification of Nanobodies

Generic Expression of Nanobodies in *E. coli*

*E. coli* TG-1 cells containing the Nanobody® constructs of interest were grown for 2 hours at 37° C. followed by 29 hours at 30° C. in baffled shaker flasks containing "5052" auto-induction medium (0.5% glycerol, 0.05% glucose, 0.2% lactose+3 mM $MgSO_4$). Overnight frozen cell pellets from *E. coli* expression cultures are then dissolved in PBS ($1/12.5^{th}$ of the original culture volume) and incubated at 4° C. for 1 hour while gently rotating. Finally, the cells are pelleted down once more and the supernatant, containing the proteins secreted into the periplasmic space, is stored.

Generic expression of Nanobodies® in *P. pastoris*

*P. pastoris* cells containing Nanobody® constructs of interest were grown for two days (at 30° C., 200 rpm) in BGCM medium. On the third day, the medium was switched to BMCM and the constructs were further grown (at 30° C., 200 rpm) and induced with 0.5% v/v methanol after 8 hours. Next day the constructs were induced with 0.5% v/v methanol in the morning, at noon and in the evening. On the fifth day, the cells are spun down and the supernatant (containing the secreted Nanobody®) is collected.

Generic Purification of Nanobodies®

HIS6-tagged Nanobodies® were purified by immobilized metal affinity chromatography (IMAC) on either Ni-Excel (GE Healthcare) or Ni-IDA/NTA (Genscript) resins with Imidazole (for the former) or acidic elution (for the latter) followed by a desalting step (PD columns with Sephadex G25 resin, GE Healthcare) and if necessary, gel filtration chromatography (Superdex column, GE Healthcare) in PBS.

3. Thermal Shift Assay

Thermal stability of the anti-FX Nanobodies® were determined using a thermal shift assay (TSA) performed in a 96-well plate on the LightCycler 480II machine (Roche). Per row, one Nanobody® was analysed according to the following pH range:

3.5/4/4.5/5/5.5/6/6.5/7/7.5/8/8.5/9. Per well, 5 μL of Nanobody® sample (0.8 mg/mL in PBS) was added to 5 μL of Sypro Orange (40× in MilliQ water; Invitrogen cat. No. S6551) and 10 μL of buffer (100 mM phosphate, 100 mM borate, 100 mM citrate and 115 mM NaCl with a pH ranging 3.5 to 9). The applied temperature gradient (37 to 99° C. at a rate of 0.03° C./s) induces unfolding of the Nanobodies, whereby their hydrophobic patches become exposed. Sypro Orange binds to those hydrophobic patches, resulting in an increase in fluorescence intensity (Ex/Em=465/580 nm). The inflection point of the first derivative of the fluorescence intensity curve at pH 7 serves as a measure of the melting temperature (Tm).

4. Analytical Size Exclusion Chromatography

Potential occurrence of aggregation and oligomerization of the Nanobodies® was investigated by analytical size exclusion chromatography (SEC). To this end, 8 µg of Nanobody® sample (0.5 mg/mL in PBS) and 10 µL of the BioRad standard (Cat. No. 151-1901, 1/10 diluted in PBS) were injected via the Dionex Ultimate 3000 equipment on a Waters Xbridge column (particle size: 3.5 µm, pore size 200 Å, ID 7.8 mm). An Arginine buffer [10 mM Phosphate+150 mM Arginine+10% 1-propanol+0.02% $NaN_3$ (pH 7.0)] was used as mobile phase and a flow-rate of 0.5 mL/minute was applied. The overall SEC behavior was determined by considering three parameters: peak area of the main peak (>90%=pass), percentage recovery (>80%=pass) and the retention time versus the 1.35 kDa BioRad standard peak.

5. Competition Assay

Antibodies (such as Nanobodies®) binding same or similar epitopes can be characterized using a competition assay which may be performed as follows.

25 µL (1 µg/mL) human plasma derived FX (Haematologic Technologies Inc, USA) is immobilised in a microtiter plate (Nunc, Wiesbaden, Germany). After washing and blocking of the wells, the "binning" mAb (mAb 00916) is added at a concentration of 1 µM in buffer containing 50 mM HEPES pH 7.4, 2.5 mM $CaCl_2$, 1% BSA and 0.05% Tween 20 (Sigma), or a reference with buffer only, and pre-incubated for 30 minutes with the coated human FX.

Subsequently test antibodies (here different Nanobodies®) are added and allowed to bind for 1 hour. Unbound test antibody (Nanobody®) and binning mAb are washed away and bound Nanobody® is detected using Horseradish Peroxidase (HRP) conjugated anti-FLAG mAb (Sigma, Cat #A8592) and a subsequent enzymatic reaction in the presence of the substrate esTMB (3,3',5,5'-tetramentylbenzidine) (SDT, Brussels, Belgium).

For the "binning" mAb, the % inhibition observed in the presence of each of the test antibody (Nanobody®) is calculated by the below equation.

$$\%\ \text{inhibition} = 100 - \left(\frac{OD450\ \text{nm test antibody (or Nanobody) at 1 uM}}{OD\ 450\ \text{nm reference}}\right) \times 100\%$$

Antibody molecules are generally considered to compete if more than 50% inhibition is observed.

Examples 1-5

Example 1: Anti-FX Nanobodies®

From the pool of anti-FX Nanobodies, a group of Nanobodies selectively binding the FX zymogen (FX and not FXa) were selected for further studies. The sequences of the Nanobodies are defined by SEQ ID NOs:8-11 and 54-57. A competition experiment with mAb 00916 (IgG1 isotype, variable sequences identified by SEQ ID NO:4 and 5) as "binning" antibody was performed and the Nanobodies Nb 701B09, Nb 701C06, Nb 702C12, Nb 701 D07, Nb 721E08, Nb 729A04, Nb 729C08 and Nb 730C03 were all shown to compete with mAb 00916. A control Nanobody®, Nb 501A02 (SEQ ID NO:12), which binds a different region of FX was also included and no competition with mAb 00916 was observed for this Nanobody®. Results are shown in table 1 below and illustrates that all compounds but Nb 501A02 compete with mAb 00916 for binding to FX, i.e. bind to the same or overlapping epitope on FX as mAb 00916.

TABLE 1

Nanobody ® (Nb) binding FX zymogen and competing with mAb 00916

| Nanobody ® ID | Competition w. mAb 00916 |
|---|---|
| Nb 701B09 (SEQ ID NO: 8) | + |
| Nb 701C06 (SEQ ID NO: 9) | + |
| Nb 702C12 (SEQ ID NO: 10) | + |
| Nb 701D07 (SEQ ID NO: 11) | + |
| Nb 501A02 (SEQ ID NO: 12) | − |
| Nb 721E08 (SEQ ID NO: 54) | + |
| Nb 729A04 (SEQ ID NO: 55) | + |
| Nb 729C08 (SEQ ID NO: 56) | + |
| Nb 730C03 (SEQ ID NO: 57) | + |

Example 2: SPR Analysis of Anti-FX Nanobody® Binding to FX

Binding of purified anti-FX Nanobodies (Nb) to human plasma-derived FX (Haematologic Technologies Inc, USA) was probed by Surface Plasmon Resonance (SPR) (Biacore T200). Briefly, anti-His mAb (MAB050 from R&D systems) was immobilised on a CM4 sensor chip using standard amine coupling chemistry. Anti-FX Nanobodies (10 nM), according to Table 3, was injected at a flow rate of 10 µL/min for 1 minute. Subsequently 4096, 1024, 256, 64, 16, 4, and 0 nM of FX were injected at a flow rate of 30 µL/min for 4 minutes to allow for binding to anti-FX Nb followed by a 5 minutes running buffer (10 mM HEPES, 150 mM NaCl, 5 mM $CaCl_2$, 0.05% (v/v) Surfactant P20, 1 mg/mL bovine serum albumin, pH 7.4) injection allowing dissociation from anti-FX Nanobody®. The running buffer was also for dilution of anti-FX Nb and FX samples. Regeneration of the chip was achieved using a regeneration buffer consisting of 3M $MgCl_2$, 30 seconds contact time, and a 30 µL/min flow rate. The binding data were collected at 25° C. and were analysed according to a 1:1 model using BiaEvaluation 4.1 supplied by the manufacturer (Biacore AB, Uppsala, Sweden).

In all cases, the binding sensograms displayed a fast on and a fast off binding kinetic profile precluding $K_D$ determination based on kinetic analysis. Therefore, the reported $K_D$ values are determined based on steady state analysis. Analysis resulted in the binding constants reported in Table 2. The strongest binder identified is Nb702C12, while the others Nanobodies® tested binds FX with a slightly higher $K_D$ and lower $R_{max}$.

TABLE 2

Estimated binding constants based on steady state analysis for the interaction of anti-FX Nanobodies ® with human plasma-derived FX as determined by SPR analysis

| FX binder | $K_D$ | $R_{max}$ |
|---|---|---|
| Nb 701B09 | 2.1 µM | 17 |
| Nb 701C06 | 0.96 µM | 14 |
| Nb 701D07 | 2.4 µM | 15 |
| Nb 702C12 | 1.2 µM | 30 |

Example 3: Activity of Anti-FX Nanobodies in FXa Generation Assay

The ability of the monovalent anti-FX Nanobody® (Nb) to promote FIXa-mediated FX-activation was determined in the presence of a procoagulant phospholipid membrane according to the principles described by Scheiflinger et al. (2008) J Thromb Haemost, 6:315-322. A Fab of mAb 13F62 (IgG1 isotype, variable sequences identified by SEQ ID NO:6 and 7), also found to bind the activation peptide, were included for comparison. Moreover, anti-FX antibodies as disclosed in U.S. Pat. No. 9,334,331 (J327 and L404-k in said publication), corresponding to the anti-FX arm of ACE910); and more recently in WO2018/021450 (J327 D31H and JYL280 in said publication) and WO2018/098363 (BIIB-12-917 represented by SEQ ID NO:427 and 615 in said publication) are stated to be suitable for use as part of anti-FIX/anti-FX bispecific FVIII mimetic compounds were, furthermore, included for comparison.

Each compound was tested individually in a concentration range from 0-1000 nM, 0-2000 nM, 0-4000 nM or 0-8000 nM by pre-incubation with 1-1.5 nM human plasma-derived FIXa (Haematologic Technologies Inc, USA) and 500 μM 25:75 phosphatidyl serine:phosphatidyl choline phospholipid vesicles (Haematologic Technologies Inc, USA) in assay buffer (50 mM HEPES, 100 mM NaCl, 5 mM $CaCl_2$, 0.1% (w/v) PEG8000, 1 mg/mL bovine serum albumin, pH 7.3) for 10 minutes. The reaction was initiated by addition of human plasma-derived FX (Haematologic Technologies Inc, USA) to a final concentration of 100 nM and a reaction volume of 50 μL. Following 20 minutes activation at room temperature while agitated (1000 RPM), the reaction was quenched by addition of 25 μL quench buffer (50 mM HEPES, 100 mM NaCl, 60 mM EDTA, 0.1% (w/v) PEG8000, 1 mg/mL bovine serum albumin, pH 7.3). The amount of FXa generated was determined by addition of 25 μL 2 mM S-2765 chromogenic substrate for FXa (Chromogenix, Sweden) and chromogenic substrate conversion was followed by measuring absorbance at 405 nm for 10 minutes in a microplate reader. The observed change in 405 nm absorbance (ΔAbs405/min) was fitted to the quadratic binding equation (eq. 1) to obtain the peak stimulatory activity and EC50.

Table 3 lists fitted maximal enhancement of FXa-generation rate (fold increase in FX-activation) and fitted $K_D$-values. Most of the tested Nanobodies stimulate FIXa-mediated FX-activation (~4 to ~83-fold relative to FIXa alone), whereas a Fab of mAb13F62 showed a 1.5 fold increased activation and Nb 501A02 showed no activation. No fitted EC50 values are provided for the Fab of 13F62 and FIXa alone.

$$Y_i = \frac{[FX] + [\text{binder}]_i + K_D - \sqrt{([FX] + [\text{binder}]_i + K_D)^2 - 4 \cdot [FX] \cdot [\text{binder}]_i}}{2 \cdot [FX]} \cdot (Y_{max} - Y_0) + Y_0 \quad \text{Eq. 1}$$

where $Y_i$ is the observed substrate conversion (ΔAbs405/min) at a given FX binder concentration (i), [FX] and [binder] is the total concentration FX and FX binder, respectively, $K_D$ is the apparent dissociation constant of the FX binder, $Y_{max}$ and $Y_0$ is the maximal and initial signal (ΔAbs405/min), respectively.

TABLE 3

Effect of FX binders on FIXa-mediated FX activation. Estimated $K_D$ (mean ± SD, n = 3) and increase in FX-activation (mean ± SD, n = 3) relative to FIXa only.

| FX binder | Estimated $K_D$ (nM) | Increase in FX activation (fold) |
|---|---|---|
| Nb 701B09 | 72.3 ± 16.3 | 83.0 ± 13.1 |
| Nb 701C06 | 41.9 ± 8.1 | 26.0 ± 6.7 |
| Nb 701D07 | 66.1 ± 25.0 | 17.2 ± 6.2 |
| Nb 702C12 | 75.4 ± 34.2 | 18.9 ± 3.0 |
| Nb 721E08 | ~1700 | >25 |
| Nb 729A04 | 83.2 ± 39.4 | 4.1 ± 0.1 |
| Nb 729C08 | ~1400 | >32 |
| Nb 730C03 | 63.9 ± 41.5 | 9.2 ± 0.3 |
| Nb 501A02 | 802 ± 505 | 0.8 ± 0.1 |
| Fab of mAb 13F62 | 3.1 ± 2.9 | 1.5 ± 0.1 |
| Fab ACE910 anti-FX (J327/L404-k)* | ~3900 | <0.6 |
| Mono-valent J327 D31H/JYL280** | 62.3 ± 52.7 | 0.45 ± 0.4 |
| Mono-valent BIIB-12-917*** | N/A | No effect |
| FIXa only | N/A | 1.0 |

N/A refers to the case where no effect on FX activation is observed when comparing absence and presence of FX binder.
In cases where FX could not be saturated with a given FX binder, and thus no plateau could be reached, the effect on FX-activation is given as "more than"/"less than" the maximum observed effect and the estimated KD is marked with "~".
*see U.S. Pat. No. 9,334,331;
**see WO2018/021450;
***see WO2018/098363

Example 4: Effect of Anti-FX Nanobodies on FXa Amidolytic Activity

To exclude that the fold increase in activation observed in example 3 could be due to a positive effect of the Nanobodies on FXa amidolytic activity the ability of the monovalent anti-FX Nanobodies to stimulate FXa amidolytic activity was investigated as follows. 5 nM human plasma-derived FIXa (Haematologic Technologies Inc, USA) was pre-incubated with 50 μM 25:75 phosphatidyl serine:phosphatidyl choline phospholipid vesicles (Haematologic Technologies Inc, USA) in assay buffer (50 mM HEPES, 100 mM NaCl, 5 mM $CaCl_2$, 0.1% (w/v) PEG8000, 1 mg/mL bovine serum albumin, pH 7.3) for 10 minutes. Human, plasma-derived FX (Haematologic Technologies Inc, USA) was added to the reaction in a final concentration of 100 nM and a final activation volume of 40 μL. After 20 minutes of incubation at room temperature while agitated (1000 RPM), the FX-activation reaction was terminated by addition of 25 quench buffer (50 mM HEPES, 100 mM NaCl, 60 mM EDTA, 0.1% (w/v) PEG8000, 1 mg/mL bovine serum albumin, pH 7.3). Hereafter, 10 μL 25 μM of the individual FX binder were added to the generated FXa before addition of 25 μL 2 mM S-2765 chromogenic substrate (Chromogenix, Sweden) and determination of chromogenic substrate conversion by measurement of absorbance at 405 nm (ΔAbs405/min) in a microplate reader. The relative FXa amidolytic activity ($a_{rel}$) is calculated using Eq. 2:

$$a_{rel} = \frac{a_{FXa\text{-}binder}}{a_{FXa}} \quad \text{Eq. 2}$$

where $a_{Fxa\text{-}binder}$ is the amidolytic activity of the FXa/FX binder complex and $a_{Fxa}$ is the amidolytic activity of FXa alone.

Table 4 shows the relative FXa amidolytic activity for the individual FX binders and it was concluded that increased FX activation could not be due to Nanobodies® having increased FXa amidolytic activity.

TABLE 4

| FXa amidolytic activity (mean ± SD, n = 2-3) in the presence of FX binders relative to free FXa | |
|---|---|
| FX binder | FXa amidolytic activity (relative to free FXa, fold) |
| Nb 701B09 | 1.06 ± 0.10 |
| Nb 701C06 | 1.06 ± 0.15 |
| Nb 701D07 | 1.05 ± 0.63 |
| Nb 702C12 | 1.05 ± 0.04 |
| Nb 721E08 | 1.07 ± 0.01 |
| Nb 729A04 | 1.11 ± 0.01 |
| Nb 729C08 | 1.09 ± 0.05 |
| Nb 730C03 | 1.01 ± 0.03 |
| mAb 13F62 | 0.94 ± 0.06 |
| Fab ACE910 anti-FX (J327/L404-k)* | 1.02 ± 0.05 |
| Mono-valent J327 D31H/JYL280** | 0.98 ± 0.004 |
| Mono-valent BIIB-12-917*** | 0.95 ± 0.02 |
| Free FXa | 1.00 ± 0.02 |

*see U.S. Pat. No. 9,334,331
**see WO2018/021450
***see WO2018/098363

Example 5: Binding Epitope of Anti-FX Nanobodies®

To determine whether the binding epitopes of anti-FX Nanobodies® and mAb 13F62 antibody are located inside the activation peptide (AP) of human FX, an ELISA assay was setup.

41 unique 12-mer peptide fragments spanning the 52 residues of the activation peptide with one amino acid spacing were immobilized in microtiter plate wells followed by incubation with the Nanobody®/antibody to be tested, and detection of bound ligand was performed by addition of a secondary HRP-labelled antibody.

The peptides were C-terminally conjugated to biotin and 50 μL of 1 μg/mL peptide solution was used for immobilization in discrete wells of the microtiter plate which was pre-coated with 1 μg/mL streptavidin. Each well was washed with washing buffer (10 mM Tris, 150 mM NaCl, 2.5 mM $CaCl_2$, 0.05% Tween 20, pH 8.60) followed by addition of 50 μL of 2 μg/mL FLAG-tagged anti-FX Nanobody® or IgG antibody to be tested. After 1 hour non-bound Nanobody®/antibody was washed off using washing buffer.

Bound anti-FX activation peptide ligand was detected by first binding a HRP-labelled secondary antibody (for FLAG-tagged Nanobodies: Anti-FLAG mAb M2-Peroxidase (HRP) (Sigma Aldrich, US), for antibody: Fcγ Fragment Specific Peroxidase AffiniPure F(ab')$_2$ Fragment Goat Anti-Human IgG (Jackson ImmunoResearch Laboratories, Inc., US), or Peroxidase AffiniPure Goat Anti-Mouse IgG (Jackson ImmunoResearch Laboratories, Inc., US)) for 1 hour, and then adding 100 μL TMB-1 ELISA substrate (Kem-En-Tec Diagnostics, Denmark).

The minimal epitopes were then deduced from the set of peptides giving rise to a signal above baseline by identifying the common sequence covered by the set of peptides (table 5) bond by each FX binder. The first residue of the epitope was defined by the last amino acid in the first consecutive, ELISA-positive peptide, while the last residue of the epitope was defined as the first residue of the last consecutive, ELISA-positive peptide.

Thus, table 5 shows ELISA signal from consecutive peptides spanning the entire FX AP for several different anti-FX Nanobodies® (Nb) and an anti-FX mAb 13F62. ELISA signals have been normalized relative to the background signal (bbg). The underlined areas marks the positive binding signals used for determining the minimal epitope.

TABLE 5

| Epitope identification | | | | | | | | | | | |
|---|---|---|---|---|---|---|---|---|---|---|---|
| Epitope residues | SEQ ID NO: | 13F62 | 701B09 | 701C06 | 701D07 | 702C12 | 501A02 | 721E08 | 729A04 | 729C08 | 730C03 |
| empty | | 1.00 | 1.00 | 1.00 | 1.00 | 1.00 | 1.00 | 1.00 | 1.00 | 1.00 | 1.00 |
| SVAQATSSSGEA | 13 | 2.55 | 0.76 | 0.92 | 0.76 | 0.96 | 0.74 | 2.25 | 0.92 | 1.14 | 1.21 |
| VAQATSSSGEAP | 14 | 2.70 | 0.73 | 0.93 | 0.84 | 1.02 | 0.88 | 2.13 | 0.99 | 1.09 | 1.24 |
| AQATSSSGEAPD | 15 | 1.89 | 0.75 | 0.91 | 0.89 | 0.97 | 0.79 | 1.92 | 1.08 | 1.17 | 1.19 |
| QATSSSGEAPDS | 16 | 1.82 | 0.77 | 0.94 | 0.81 | 0.96 | 0.82 | 1.97 | 1.08 | 1.12 | 1.14 |
| ATSSSGEAPDSI | 17 | 3.20 | 0.82 | 0.91 | 0.86 | 0.98 | 0.82 | 2.27 | 1.24 | 1.13 | 1.19 |
| TSSSGEAPDSIT | 18 | 0.68 | 0.97 | 0.87 | 0.75 | 0.77 | 0.76 | 2.20 | 1.12 | 1.06 | 1.20 |
| SSSGEAPDSITW | 19 | 0.77 | 0.84 | 0.90 | 0.73 | 0.86 | 0.82 | 1.99 | 1.24 | 1.10 | 1.21 |
| SSGEAPDSITWK | 20 | 0.73 | 0.89 | 0.89 | 0.74 | 0.88 | 0.71 | 2.01 | 0.96 | 1.06 | 1.22 |
| SGEAPDSITWKP | 21 | 0.82 | 0.84 | 0.88 | 0.78 | 0.88 | 0.76 | 2.15 | 0.98 | 1.07 | 1.18 |
| GEAPDSITWKPY | 22 | 1.50 | 0.86 | 0.90 | 0.80 | 0.93 | 0.94 | 2.26 | 1.05 | 1.15 | 1.24 |
| EAPDSITWKPYD | 23 | 1.64 | 0.79 | 0.89 | 0.76 | 0.97 | 0.76 | 2.35 | 1.01 | 1.11 | 1.24 |
| APDSITWKPYDA | 24 | 1.59 | 0.82 | 0.96 | 0.90 | 1.06 | 0.74 | 2.29 | 1.04 | 1.09 | 1.16 |
| PDSITWKPYDAA | 25 | 1.89 | 0.83 | 0.92 | 0.84 | 1.05 | 0.79 | 2.40 | 0.95 | 1.17 | 1.24 |

TABLE 5 -continued

| Epitope identification | | | | | | | | | | | |
|---|---|---|---|---|---|---|---|---|---|---|---|
| Epitope residues | SEQ ID NO: | 13F62 | 701B09 | 701C06 | 701D07 | 702C12 | 501A02 | 721E08 | 729A04 | 729C08 | 730C03 |
| DSITWKPYDAAD | 26 | 3.61 | 0.76 | 0.93 | 0.89 | 1.08 | 0.79 | 2.18 | 1.05 | 1.09 | 1.22 |
| SITWKPYDAADL | 27 | 7.95 | 0.84 | 0.94 | 1.04 | 1.08 | 0.71 | 2.28 | 1.13 | 1.11 | 1.18 |
| ITWKPYDAADLD | 28 | 4.23 | 0.83 | 1.03 | 0.89 | 1.10 | 0.74 | 2.08 | 1.28 | 1.06 | 1.20 |
| TWKPYDAADLDP | 29 | 1.95 | 0.92 | 1.00 | 0.91 | 1.13 | 0.74 | 2.26 | 0.99 | 1.17 | 1.26 |
| WKPYDAADLDPT | 30 | 1.18 | 1.14 | 0.99 | 0.85 | 0.89 | 0.74 | 1.83 | 1.20 | 1.08 | 1.14 |
| KPYDAADLDPTE | 31 | 0.77 | 0.88 | 0.90 | 0.73 | 0.80 | 0.82 | 1.89 | 1.33 | 1.10 | 1.17 |
| PYDAADLDPTEN | 32 | 0.84 | 0.88 | 0.82 | 0.73 | 0.83 | 0.79 | 2.05 | 1.06 | 1.08 | 1.20 |
| YDAADLDPTENP | 33 | 0.84 | 0.81 | 0.85 | 0.75 | 0.87 | 0.71 | 2.21 | 1.06 | 1.09 | 1.28 |
| DAADLDPTENPF | 34 | 0.77 | 0.81 | 0.85 | 0.70 | 0.88 | 0.88 | 2.30 | 1.10 | 1.18 | 1.24 |
| AADLDPTENPFD | 35 | 0.77 | 0.79 | 0.82 | 0.69 | 0.88 | 0.79 | 2.22 | 1.05 | 1.17 | 1.21 |
| ADLDPTENPFDL | 36 | 1.25 | 0.73 | 0.87 | 0.77 | 0.91 | 0.71 | 2.34 | 0.98 | 1.11 | 1.25 |
| DLDPTENPFDLL | 37 | 26.45 | 0.82 | 0.88 | 0.74 | 1.00 | 0.79 | 2.48 | 1.06 | 1.21 | 1.26 |
| LDPTENPFDLLD | 38 | 31.00 | 0.84 | 0.94 | 0.80 | 1.11 | 0.91 | 2.29 | 1.91 | 1.58 | 1.30 |
| DPTENPFDLLDF | 39 | 29.75 | 2.87 | 1.51 | 1.39 | 4.16 | 0.88 | 2.27 | 4.03 | 1.95 | 1.68 |
| PTENPFDLLDFN | 40 | 30.11 | 3.91 | 1.61 | 1.29 | 4.58 | 0.88 | 2.35 | 5.18 | 2.06 | 1.62 |
| TENPFDLLDFNQ | 41 | 29.68 | 4.38 | 1.74 | 1.44 | 4.84 | 1.09 | 2.54 | 9.12 | 3.14 | 2.10 |
| ENPFDLLDFNQT | 42 | 28.68 | 3.43 | 1.56 | 1.27 | 4.00 | 0.82 | 2.88 | 17.83 | 8.06 | 6.57 |
| NPFDLLDFNQTQ | 43 | 28.61 | 2.16 | 1.29 | 0.96 | 3.13 | 0.94 | 2.28 | 8.27 | 3.41 | 2.82 |
| PFDLLDFNQTQP | 44 | 29.73 | 3.48 | 1.50 | 1.13 | 4.95 | 0.79 | 2.50 | 1.41 | 1.18 | 1.23 |
| FDLLDFNQTQPE | 45 | 30.57 | 3.27 | 1.41 | 0.99 | 4.38 | 0.85 | 3.01 | 1.58 | 1.15 | 1.28 |
| DLLDFNQTQPER | 46 | 0.82 | 1.17 | 1.13 | 0.81 | 3.08 | 0.76 | 2.45 | 1.12 | 1.22 | 1.18 |
| LLDFNQTQPERG | 47 | 0.86 | 1.09 | 1.03 | 0.80 | 1.88 | 0.79 | 2.30 | 1.10 | 1.13 | 1.10 |
| LDFNQTQPERGD | 48 | 0.80 | 0.82 | 0.93 | 0.79 | 0.97 | 0.74 | 2.21 | 0.98 | 1.12 | 1.14 |
| DFNQTQPERGDN | 49 | 1.23 | 0.87 | 0.87 | 0.75 | 0.94 | 0.71 | 2.25 | 0.97 | 1.10 | 1.16 |
| FNQTQPERGDNN | 50 | 1.77 | 0.89 | 0.88 | 0.82 | 1.00 | 0.71 | 2.16 | 1.05 | 1.08 | 1.16 |
| NQTQPERGDNNL | 51 | 2.45 | 0.79 | 0.85 | 0.87 | 0.92 | 0.71 | 2.02 | 1.13 | 1.09 | 1.22 |
| QTQPERGDNNLT | 52 | 1.95 | 0.72 | 0.93 | 0.79 | 0.88 | 0.76 | 1.96 | 1.11 | 1.04 | 1.10 |
| TQPERGDNNLTR | 53 | 8.86 | 0.93 | 0.97 | 0.88 | 1.05 | 0.85 | 1.97 | 1.09 | 1.37 | 1.06 |

The minimal epitope was defined as the amino acid sequence in common between the ELISA positive peptides for each FX binder. The determined minimal epitopes within AP is summarized in table 6.

TABLE 6

| Minimal epitope sequences for the anti-FX Nanobodies ® and mAb13F62 | | |
|---|---|---|
| FX binder | Epitope in AP | Minimal epitope sequence |
| Nb 701B09 | 33-38 | FDLLDF |
| Nb 701C06 | 33-38 | FDLLDF |

TABLE 6-continued

| Minimal epitope sequences for the anti-FX Nanobodies ® and mAb13F62 | | |
|---|---|---|
| FX binder | Epitope in AP | Minimal epitope sequence |
| Nb 701D07 | 32-38 | PFDLLDF |
| Nb 702C12 | 35-38 | LLDF |
| Nb 721E08 | 33-40 | FDLLDFNQ |
| Nb 729A04 | 33-37 | FDLLD |
| Nb 729C08 | 31-37 | NPFDLLD |

TABLE 6-continued

| Minimal epitope sequences for the anti-FX Nanobodies ® and mAb13F62 | | |
|---|---|---|
| FX binder | Epitope in AP | Minimal epitope sequence |
| Nb 730C03 | 31-38 | NPFDLLDF |
| mAb13F62 | 33-36 | FDLL |
| Nb 501A02 | No epitope in AP detected | |

By correlating the data of tables 5 and 6 with the data of table 3, it is observed that the ability to stimulate FX activation is observed for FX binders for which the minimal epitope on FX for example is “PFDLLDF”.

It follows from Table 6 that a common minimal epitope can be identified as ‘LL’.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A single domain antibody capable of binding FX, comprising SEQ ID NO:8, 9, 10, 11, 54, 55, 56 or 57, respectively; or comprising the three CDRs of SEQ ID NO:8, 9, 10, 11, 54, 55, 56 or 57, respectively.

2. The single domain antibody according to claim 1, comprising SEQ ID NO:8, 9, 10, 11, 54, 55, 56 or 57, respectively.

3. The single domain antibody according to claim 1, comprising the three CDRs of SEQ ID NO:8, 9, 10, 11, 54, 55, 56 or 57, respectively.

4. The single domain antibody according to claim 2, wherein the single domain antibody is a VHH, a humanized VHH, or a camelized VH domain.

5. The single domain antibody according to claim 3, wherein the single domain antibody is a VHH, a humanized VHH, or a camelized VH domain.

6. A method of treating a haemophilia, comprising administering the single domain antibody according to claim 1 to a subject in need thereof.

7. The method of claim 6, wherein haemophilia is haemophilia A with inhibitors, haemophilia A without inhibitors, haemophilia B with inhibitors, or haemophilia B without inhibitors.

* * * * *